(12) United States Patent
Scherz et al.

(10) Patent No.: US 8,461,142 B2
(45) Date of Patent: Jun. 11, 2013

(54) WATER-SOLUBLE ANIONIC BACTERIOCHLOROPHYLL DERIVATIVES AND THEIR USES

(75) Inventors: Avigdor Scherz, Rehovot (IL); Alexander Brandis, Rehovot (IL); Ohad Mazor, Lod (IL); Yoram Salomon, Rehovot (IL); Hugo Scheer, Blonhofen (DE)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 12/942,938

(22) Filed: Nov. 9, 2010

(65) Prior Publication Data

US 2011/0117029 A1 May 19, 2011

Related U.S. Application Data

(63) Continuation of application No. 10/534,692, filed as application No. PCT/IL03/00973 on Nov. 17, 2003, now Pat. No. 7,947,672.

(30) Foreign Application Priority Data

Nov. 17, 2002 (IL) .......................................... 152900

(51) Int. Cl.
| | |
|---|---|
| *A01N 55/02* | (2006.01) |
| *A61K 31/40* | (2006.01) |
| *C07D 487/02* | (2006.01) |
| *A61B 5/00* | (2006.01) |

(52) U.S. Cl.
USPC ........ 514/185; 514/410; 540/145; 424/9.362; 424/9.61

(58) Field of Classification Search
USPC ................. 540/145; 514/185, 410; 424/9.362, 424/9.81
See application file for complete search history.

(56) References Cited

U.S. PATENT DOCUMENTS

| | | | |
|---|---|---|---|
| 4,512,762 A | 4/1985 | Spears | |
| 5,004,811 A | 4/1991 | Bommer et al. | |
| 5,726,169 A | 3/1998 | Scherz et al. | |
| 5,955,585 A * | 9/1999 | Scherz et al. | 530/408 |
| 6,147,195 A * | 11/2000 | Scherz et al. | 530/391.1 |
| 6,569,846 B1 | 5/2003 | Scherz et al. | |

FOREIGN PATENT DOCUMENTS

| | | |
|---|---|---|
| DE | 4121876 A1 | 1/1993 |
| JP | 9-110872 A | 4/1997 |
| JP | 2001-342190 A | 12/2001 |
| WO | WO 88/07988 A1 | 10/1988 |
| WO | WO 90/12573 A1 | 11/1990 |
| WO | WO 94/00118 A1 | 1/1994 |
| WO | WO 97/19081 A1 | 5/1997 |
| WO | WO 00/33833 A1 | 6/2000 |
| WO | WO 01/40232 A1 | 6/2001 |
| WO | WO 02/13820 A1 | 2/2002 |
| WO | WO 02/098882 A1 | 12/2002 |

OTHER PUBLICATIONS

Hargus et al., 2007, "Mono-(L)-aspartylcholrin-$e_6$," *Photochem. Photobiol*, 83:1006-1015.
Wooley et al., 1998, "A Comparative Study of the Allomerization Reaction of Cholorphyll α and Bactreriochlorophyll α," *J. Chem. Soc., Perkin Trans. 2*, pp. 1833-1839.
Ashur et al., 2009, "Photocatalytic Generation of Oxygen Radicals by the Water-Soluble Bacteriochlorophyll Derivative WST-11, Noncovalently Bound to Serum Albumin," *J. Phys. Chem. A* 113:8027-8037.
Banker et al., 1996, "Modern Pharmaceuticals," 3rd Edition, p. 596.
Brandis et al., 2005, "Novel Water-soluble Bacteriochlorophyll Derivatives for Vascular-targeted Photodynamic Therapy: Synthesis, solubility, Phototoxicity and the Effect of Serum Proteins," *Photochem. Photobiol.* 81: 983-993.
Chen et al., 2002, "Preclinical Studies in Normal Canine Prostate of a Novel Palladium-Bacteriopheophorbide (WST09) Photosensitizer for Photodynamic Therapy of Prostate Cancers," *Photochem. Photobiol.* 76(4):438-445.
Dagan et al., 1995, "Uptake by cells and photosensitizing effectiveness of novel pheophorbide derivatives in vitro," *Int. J Cancer*, 63(6):831-839.
Dandler et al., 2010, "Distribution of Chlorophyll- and Bacteriochlorophyll-derived Photosensitizers in Human Blood Plasma," *Photochem. Photobiol.* 86:182-193.
Ellsworth et al., 1978, "Methyl 10-epipheophorbide a: an unusual epimeric stability relative to chlorophyll a or a' ", *J. Organic Chem.* 43(2):281-283.
Koudinova et al., 2003, "Photodynamic Therapy with Pd-Bacteriopheophorbide (TookAD): Successful in Vivo Treatment of Human Prostatic Small Cell Carcinoma Xenografts," *Int. J. Cancer* 104(6):782-789.
Ma et al., 1996, "Nucleophilic reaction of 1,8-diazabicyclo[5.4.0]undec-7-ene and 1,5-diazabicyclo[4.3.0]non-5-ene with methyl pheophorbide a. Unexpected products," *Tetrahedron* 52(3):849-860.
Mazor et al., 2005, "WST-11, A Novel Water-soluble Bacteriochlorophyll Derivative; Cellular Uptake, Pharmacokinetics, Biodistribution and Vascular-targeted Photodynamic Activity Using melanoma Tumors as a Model," *Photochem. Photobiol.* 81:342-351.
McMahon, 2000, "VEGF Receptor Signaling in Tumor Angiogenesis," *The Oncologist* 5(suppl 1):3-10 (www.TheOncologist.com).

(Continued)

*Primary Examiner* — Paul V. Ward
(74) *Attorney, Agent, or Firm* — Dechert LLP

(57) ABSTRACT

The invention provides anionic water-soluble tetracyclic and pentacyclic bacteriochlorophyll derivatives (Bchls) containing at least one, preferably two or three, negatively charged groups and/or acidic groups that are converted to negatively charged groups at the physiological pH, preferably Bchls having a group COO<–>, COS<–>, SO3<–>, PO3<2–>, COOH, COSH, SO3H, and/or PO3H2 bound through an ester or amide bond to one or more of the positions 17<3>, 13<3>, and 3<2> of the tetracyclic or pentacyclic Bchl molecule, for photodynamic therapy and diagnosis.

26 Claims, 8 Drawing Sheets

OTHER PUBLICATIONS

"Nomenclature of Tetrapyrroles: TP-4 Reduced Porphyrins Including Cholrins," http:/www.chemqmul.ac.uk/iupac/tetrapyrrole/TP4.html (last 6 pages), downloaded Feb. 2, 2009.

Pinedo et al., 2000, "Translational Research: The Role of VEGF in Tumor Angiogenesis," *The Oncologist* 5(suppl 1):3-10 (www.TheOncologist.com).

Rosenbach-Belkin et al., 1996, "Serine Conjugates of Chlorophyll and Bacteriochlorophyll: Photocytotoxicity in Vitro and Tissue Distribution in Mice Bearing Melanoma Tumors," *Photochem. Photobiol.* 64(1):174-181.

Schreiber et al., 2002, "Local Photodynamic Therapy (PDT) of Rat C6 Glioma Xenografts with Pd-Bacteriopheophorbide Leads to Decreased Metastases and Increase of Animal Cure Compared with Surgery," *Int. J. Cancer* 99(2):279-285.

Wolf, 1995, "Burger's Medicinal Chemistry," 5$^{th}$ Edition, Part 1, pp. 975-977.

Zilberstein et al., 1997, "Light-Dependant Oxygen Consumption in Bacteriochlorophyll-Serine-Treated Melanoma Tumors: On-line Determination Using a Tissue-Inserted Oxygen Microsensor," *Photochem. Photobiol.* 65(6):11012-1019.

Zilberstein et al., 2001, "Antivascular Treatment of Solid Melanoma Tumors with Bacteriochlorophyll-Serine-Based Photodynamic Therapy," *Photochem. Photobiol.* 73(3):257-266.

\* cited by examiner

WATER-SOLUBLE ANIONIC BACTERIOCHLOROPHYLL DERIVATIVES AND THEIR USES

CROSS-REFERENCE TO RELATED APPLICATIONS

This application is a continuation of application Ser. No. 10/534,692, filed Nov. 9, 2005, now U.S. Pat. No. 7,947,672 which is the US national stage under 35 U.S.C. §371 of international application no. PCT/IL2003/000973, filed Nov. 17, 2003, which claims priority under 35 U.S.C. §§119(a)-(d) and 365(b) to Israeli application no. 152900, filed Nov. 17, 2002.

FIELD OF THE INVENTION

The present invention relates to novel water-soluble anionic derivatives of bacteriochlorophyll, to their preparation and their use in methods of in-vivo photodynamic therapy and diagnosis of tumors and different vascular diseases such as age-related macular degeneration, as well as in methods of in-vivo and ex-vivo killing of viruses and microorganisms.

DEFINITIONS AND ABBREVIATIONS

AMD: age-related macular degeneration;
Bchl: bacteriochlorophyll a-pentacyclic 7,8,17,18-tetrahydroporphyrin with a $5^{th}$ isocyclic ring, a central Mg atom, a phytyl or geranylgeranyl group at position $17^3$, a $COOCH_3$ group at position $13^2$, an H atom at position $13^2$, methyl groups at positions
2, 7, 12, 18, an acetyl group at position 3, and an ethyl group at position 8;
Bphe: bacteriopheophytin a (Bchl in which central Mg is replaced by two H atoms);
Bpheid: bacteriopheophorbide a (the $C-17^2$-free carboxylic acid derived from BPhe);
Pd-Bpheid: Pd-bacteriopheophorbide a;
PDT: photodynamic therapy;
Rhodobacteriochlorin: tetracyclic 7,8,17,18-tetrahydroporphyrin having a —$CH_2CH_2COOH$ group at position 17, a —COOH at position 13, methyl groups at positions 2, 7, 12, 18, and ethyl groups at positions 3 and 8.

IUPAC numbering of the bacteriochlorophyll derivatives is used throughout the specification. Using this nomenclature, the natural bacteriochlorophylls carry two carboxylic acid esters at positions $13^2$ and $17^2$, however they are esterified at positions $13^3$ and $17^3$.

BACKGROUND OF THE INVENTION

Photodynamic therapy (PDT) is a non-surgical treatment of tumors in which non-toxic drugs and non-hazardous photosensitizing irradiation are combined to generate cytotoxic reactive oxygen species in situ. This technique is more selective than the commonly used tumor chemotherapy and radiotherapy. To date, porphyrins have been employed as the primary photosensitizing agents in clinics. However, current sensitizers suffer from several deficiencies that limit their application, including mainly: (1) relatively weak absorption in the visible spectral range which limits the treatment to shallow tumors; (2) accumulation and long retention of the sensitizer in the patient skin, leading to prolonged (days to months) skin phototoxicity; and (3) small or even no differentiation between the PDT effect on illuminated tumor and non-tumor tissues. The drawbacks of current drugs inspired an extensive search for long wavelength absorbing second-generation sensitizers that exhibit better differentiation between their retention in tumor cells and skin or other normal tissues.

In order to optimize the performance of the porphyrin drugs in therapeutics and diagnostics, several porphyrin derivatives have been proposed in which, for example, there is a central metal atom (other than Mg) complexed to the four pyrrole rings, and/or the peripheral substituents of the pyrrole rings are modified and/or the macrocycle is dihydrogenated to chlorophyll derivatives (chlorins) or tetrahydrogenated to bacteriochlorophyll derivatives (bacteriochlorins).

Due to their intense absorption in favorable spectral regions (650-850 nm) and their ready degradation after treatment, chlorophyll and bacteriochlorophyll derivatives have been identified as excellent sensitizers for PDT of tumors and to have superior properties in comparison to porphyrins, but they are less readily available and more difficult to handle.

Bacteriochlorophylls are of potential advantage compared to the chlorophylls because they show intense near-infrared bands, i.e. at considerably longer wavelengths than chlorophyll derivatives.

The spectra, photophysics, and photochemistry of native bacteriochlorophylls (Bchls) have made them optimal light-harvesting molecules with clear advantages over other sensitizers presently used in PDT. In particular, these molecules have a very high extinction coefficient at long wavelengths ($\lambda_{max}$=760-780 nm, $\epsilon$=(4-10)×$10^4$ $M^{-1}$ $cm^{-1}$), where light penetrates deeply into tissues. They also generate reactive oxygen species (ROS) at a high quantum yield (depending on the central metal).

Under normal delivery conditions, i.e. in the presence of oxygen at room temperature and under normal light conditions, the BChl moieties are labile and have somewhat lower quantum yields for triplet state formation, when compared with, e.g., hematoporphyrin derivative (HPD). However, their possible initiation of biological redox reactions, favorable spectral characteristics and their ready degradation in vivo result in the potential superiority of bacteriochlorophylls over other compounds, e.g. porphyrins and chlorophylls, for PDT therapy and diagnostics and for killing of cells, viruses and bacteria in samples and in living tissue. Chemical modification of bacteriochlorophylls is expected to further improve their properties, but this has been very limited due to lack of suitable methods for the preparation of such modified bacteriochlorophylls.

The biological uptake and PDT efficacy of metal-free derivatives of Bchl have been studied with the objective to manipulate the affinity of the sensitizers to the tumor cellular compartment. Cardinal to this approach is the use of highly lipophilic drugs that may increase the accumulation of the drug in the tumor cells, but also renders its delivery difficult. In addition, the reported biodistribution shows significant phototoxic drug levels in non-tumor tissues over prolonged periods (at least days) after administering the drug.

In applicant's previous Israel Patent No. 102645 and corresponding EP 0584552, U.S. Pat. No. 5,726,169, U.S. Pat. No. 5,726,169, U.S. Pat. No. 5,955,585 and U.S. Pat. No. 6,147,195, a different approach was taken by the inventors. Highly efficient anti-vascular sensitizers that do not extravasate from the circulation after administration and have short lifetime in the blood were studied. It was expected that the inherent difference between vessels of normal and abnormal tissues such as tumors or other tissues that rely on neovessels, would enable relatively selective destruction of the abnormal tissue. Hence, it was aimed to synthesize Bchl derivatives that are more polar and, hence, have better chance to stay in the vascular compartment, where they convey the primary photodynamic effect. To this end, the geranylgeranyl residue at the C-17 position of Bchl a (Compound 1, depicted in Scheme 1 herein) has been replaced by various residues such as amino acids, peptides, or proteins, which enhance the sensitizer hydrophilicity. One particular derivative, Bchl-Ser (Scheme 1, Compound 1, wherein R is seryl), was found to be water-soluble and highly phototoxic in cell cultures. Following intraperitoneal injection, the Bchl-Ser cleared from the mouse blood and tissues bi-exponentially in a relatively short time ($t_{1/2}$ ~2 and 16 h, respectively). Clearance from the circulation was even faster following intravenous injection. Under the selected treatment protocol (light application within minutes after drug injection), phototoxicity was predominantly conferred to the tumor vasculature (Rosenbach-Belkin et al., 1996; Zilberstein et al., 2001 and 1997). However, unfortunately, like native Bchl, the Bchl-Ser derivative undergoes rapid photo-oxidation, forming the corresponding 2-desvinyl-2-acetyl-chlorophyllide ester and other products.

To increase the stability of the Bchl derivatives, the central Mg atom was replaced by Pd in the later applicant's PCT Publication WO 00/33833 and U.S. Pat. No. 6,569,846. This heavy atom was previously shown to markedly increase the oxidation potential of the Bchl macrocycle and, at the same time, to greatly enhance the intersystem-crossing (ISC) rate of the molecule to its triplet state. The metal replacement was performed by direct incorporation of $Pd^{2+}$ ion into a Bpheid molecule, as described in WO 00/33833. Based on the pigment biodistribution and pharmacokinetics, it was assumed that the derivative Pd-Bpheid remained in the circulation for a very short time with practically no extravasation to other tissues, and is therefore a good candidate for vascular-targeting PDT that avoids skin phototoxicity. The treatment effect on the blood vessels was demonstrated by intravital microscopy of treated blood vessels and staining with Evans-Blue. Using a treatment protocol with a minimal drug-to-light interval, Pd-Bpheid (also designated Tookad) was found to be effective in the eradication of different tumors in mice, rats and other animal models and is presently entering Phase I/II clinical trials in patients with prostate cancer that failed radiation therapy (Chen et al., 2002; Schreiber et al., 2002; Koudinova et al., 2003).

Because of its low solubility in aqueous solutions, the clinical use of Pd-Bpheid requires the use of solubilizing agents such as Cremophor that may cause side effects at high doses. It would be highly desirable to render the Pd-Bpheid water-soluble while retaining its physico-chemical properties. Alternatively, it would be desirable to prepare Bchl derivatives that are cytophototoxic and, at the same time, more water-soluble than Pd-Bpheid itself. Such water solubility is expected to further enhance the drug retention in the circulation and, thereby, the aforementioned selectivity. In addition, having no need to use carriers such as detergents or lyposomes, may prevent side effects.

SUMMARY OF THE INVENTION

The present invention relates to a bacteriochlorophyll derivative containing at least one, preferably two or three, negatively charged groups and/or acidic groups that are converted to negatively charged groups at the physiological pH, excluding pentacyclic bacteriochlorophyll derivatives having a free $CH_2CH_2COOH$ or a $CH_2CH_2COO^-$ group at position 17, and tetracyclic bacteriochlorophyll derivatives devoid of a central metal atom and having a —$CH_2CH_2COOH$ group at position 17, a —$CH_2COOH$ or —COOH group at position 15, a —COOH group at position 13, methyl groups at the positions 2, 7, 12, 18, and ethyl groups at the positions 3 and 8.

The negatively charged groups according to the invention include, but are not limited to, carboxylate ($COO^-$), thiocarboxylate ($COS^-$), sulfonate ($SO_3^-$), and phosphonate ($PO_3^{2-}$), and the acidic groups from which said charged groups originate at the physiological pH are the carboxylic (COOH), thiocarboxylic (COSH), sulfonic ($SO_3H$) and phosphonic ($PO_3H_2$) acid groups, respectively.

In one embodiment, the bacteriochlorophyll derivative has the formula I or II:

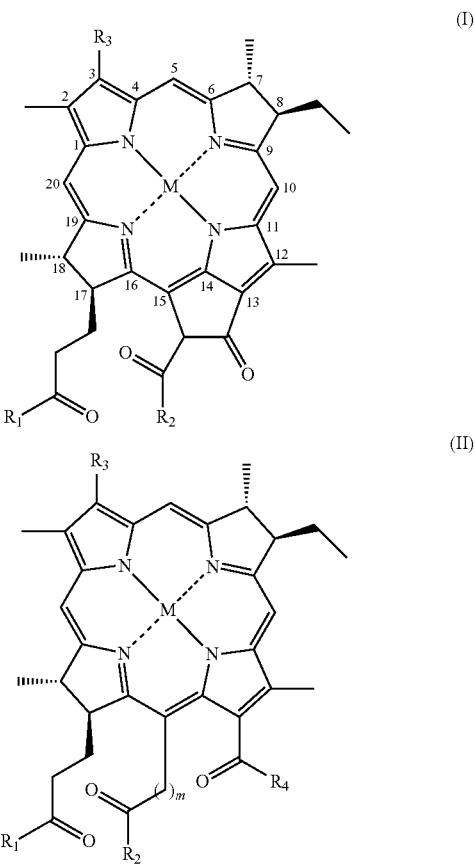

wherein

M represents 2H or a metal atom selected from the group consisting of divalent Pd, Pt, Co, Sn, Ni, Cu, Zn and Mn, and trivalent Fe, Mn and Cr;

$R_1$; $R_2$, and $R_4$ each independently is Y—$R_5$;

Y is O, S or $NR_5R_6$;

$R_3$ is selected from the group consisting of —CH=$CH_2$, —C(=O)—$CH_3$, —C(=O)—H, —CH=$NR_7$, —C($CH_3$)=$NR_7$, —$CH_2$—$OR_7$, —$CH_2$—$SR_7$, —$CH_2$—$NR_7R'_7$, —CH($CH_3$)—$OR_7$, —CH($CH_3$)—$SR_7$, —CH($CH_3$)—$NR_7R'_7$, —CH($CH_3$)Hal, —$CH_2$-Hal, —$CH_2$—$R_7$, —CH=$CR_7CR_7R'_7$, —C($CH_3$)=$CR_7R'_7$, —CH=$CR_7$Hal, —C($CH_3$)=$CR_7$Hal, and —C≡$CR_7$;

$R_5$, $R_6$, $R_7$ and $R'_7$ each independently is H or selected from the group consisting of:

(a) $C_1$-$C_{25}$ hydrocarbyl optionally containing one or more heteroatoms, carbocyclic or heterocyclic moieties, and/or optionally substituted by one or more functional groups selected from the group consisting of halogen, oxo, OH, SH, CHO, $NH_2$, $CONH_2$, a negatively charged group, and an acidic group that is converted to a negatively charged group at the physiological pH;

(b) a residue of an amino acid, a peptide or of a protein; and (c) when Y is O or S; $R_5$ may further be $R_8^+$;

m is 0 or 1; and $R_8^+$ is $H^+$ or a cation;

provided that:

(i) at least one, preferably two, of $R_5$, $R_6$, $R_7$ and $R'_7$ is a hydrocarbon chain as defined in (a) above substituted by a negatively charged group or by an acidic group that is converted to a negatively charged group at the physiological pH; or (ii) at least one, preferably two, of $R_1$, $R_2$, and $R_4$ is OH, SH, $O^-R_8^+$ or $S^-R_8^+$;

(iii) at least one of $R_1$, $R_2$, and $R_4$ is OH, SH, $O^-R_8^+$ or $S^-R_8^+$ and at least one of $R_5$, $R_6$, $R_7$ and $R'_7$ is a hydrocarbon chain substituted by a negatively charged group or by an acidic group that is converted to a negatively charged group at the physiological pH; or (iv) at least one of $R_1$, $R_2$, and $R_4$ is OH, SH, $O^-R_8^+$ or $S^-R_8^+$ and at least one of $R_5$, $R_6$, $R_7$ and $R'_7$ is a residue of an amino acid, a peptide or of a protein; or (v) at least one of $R_5$, $R_6$, $R_7$ and $R'_7$ is a hydrocarbon chain substituted by a negatively charged group or by an acidic group that is converted to a negatively charged group at the physiological pH and at least one of $R_5$, $R_6$, $R_7$ and $R'_7$ is a residue of an amino acid, a peptide or of a protein;

but excluding the compounds of formula I wherein M is as defined, $R_3$ is —C(=O)$CH_3$, $R_1$ is OH or $OR_8^+$ and $R_2$ is —$OCH_3$, and the compound of formula II wherein M is 2H, $R_3$ is —C(=O)$CH_3$, $R_1$, $R_2$ and $R_4$ are OH, and m is 0 or 1.

The invention further relates to pharmaceutical compositions comprising a bacteriochlorophyll derivative as defined above for photodynamic therapy (PDT), particularly for vascular-targeting PDT, for example for PDT of tumors or of age-related macular degeneration (AMD), or for killing cells or infectious agents comprising bacteria and viruses in vivo or in vitro, as well as for diagnostic purposes.

The invention provides a method for photodynamic therapy using a photosensitizer, wherein the improvement consists in that said photosensitizer is a bacteriochlorophyll derivative of the invention. According to this aspect, the invention relates to a method for treatment by PDT which comprises administering to an individual in need an effective amount of a bacteriochlorophyll derivative of the invention, followed by local irradiation.

The invention further provides a method for diagnosis of tumors using a photosensitizer, wherein the improvement consists in that said photosensitizer is a bacteriochlorophyll derivative of the invention. According to this aspect, the invention relates to a method for diagnosis of tumors which comprises administering to an individual suspected of having a tumor an effective amount of a bacteriochlorophyll derivative of the invention, followed by local irradiation and measuring the fluorescence of the suspected area, wherein a higher fluorescence indicates tumor sites.

The invention still further provides a method for killing cells or infectious agents comprising bacteria and viruses, using a photosensitizer, the improvement wherein said photosensitizer is a bacteriochlorophyll derivative of the invention. According to this aspect, the invention relates to a method for sterilization of biological products, e.g. blood, which comprises adding to said biological product, e.g. blood, an effective amount of a bacteriochlorophyll derivative of the invention, followed by irradiation.

BRIEF DESCRIPTION OF THE FIGURES

The different compounds of the invention are represented in the following description of the drawings by a bold and underlined numeral. Their full identification is found in the List of Compounds at the beginning of the Chemical Section hereinafter.

DETAILED DESCRIPTION OF THE INVENTION

Figure 1A:
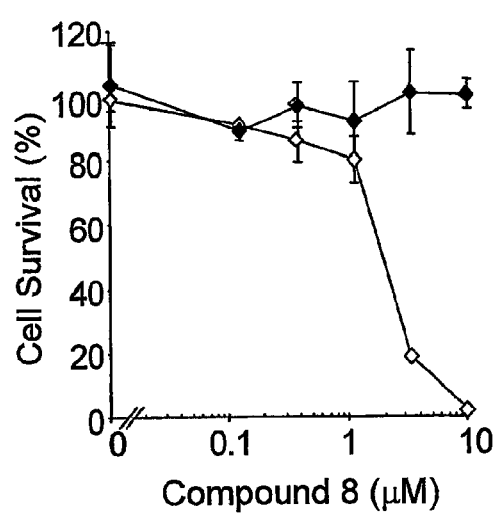
FIGS. 1A-1B are graphs showing the phototoxicity of the sulfonated compound 8 on H5V mouse endothelial cells (FIG. 1A) and M2R mouse melanoma cells (FIG. 1B). Cells were incubated with increasing concentrations of 8 for 4 hours, washed and illuminated (open shapes) or kept in the dark (dark control, closed shapes). Points are average of triplicates±STD.

The present invention provides, in a broad aspect, bacteriochlorophyll derivatives containing at least one, preferably two or three, negatively charged groups and/or acidic groups that are converted to negatively charged groups at the physiological pH, excluding pentacyclic bacteriochlorophyll derivatives having a free —$CH_2CH_2COOH$ or —$CH_2CH_2COO^-$ group at position 17, and tetracyclic bacteriochlorophyll derivatives devoid of a central metal atom and having a —$CH_2CH_2COOH$ group at position 17, a —$CH_2COOH$ or —COOH group at position 15, a —COOH group at position 13, a methyl group at each of the positions 2, 7, 12, and 18, and an ethyl group at each of the positions 3 and 8.

The bacteriochlorophyll derivatives may be derived from a natural or synthetic derivative of bacteriochlorophyll, including compounds in which the central Mg atom has been deleted or replaced by other metal atoms such as divalent Pd, Pt, Co, Sn, Ni, Cu, Zn and Mn, and trivalent Fe, Mn and Cr. In preferred embodiments, the metal atom is absent or it is Pd, Cu, Zn or Mn. In the most preferred embodiment, the central metal atom is Pd.

In one preferred embodiment, the present invention provides a bacteriochlorophyll derivative of the formula I or II as defined hereinabove.

According to the invention, "hydrocarbyl" as defined for $R_5$, $R_6$, $R_7$ and $R'_7$ means any straight or branched, saturated or unsaturated, acyclic or cyclic, including aromatic, hydrocarbyl radicals, of 1-25 carbon atoms, preferably of 1 to 20, more preferably 1 to 6, most preferably 2-3 carbon atoms. The hydrocarbyl may be an alkyl radical, preferably of 1-4 carbon atoms, e.g. methyl, ethyl, propyl, butyl, or alkenyl, alkynyl, cycloalkyl, aryl such as phenyl or an aralkyl group such as benzyl, or at the position 17 it is a radical derived from natural Chl and Bchl compounds, e.g. geranylgeranyl (2,6-dimethyl-2,6-octadienyl) or phytyl (2,6,10,14-tetramethyl-hexadec-14-en-16-yl).

The hydrocarbon chain of $R_5$, $R_6$, $R_7$ and/or $R'_7$ may optionally contain one or more heteroatoms such as O, S and/or NH, and/or one or more carbocyclic ring, e.g. phenyl, or heterocyclic ring, e.g pyridyl, moieties. In one embodiment, the hydrocarbyl chain contains one or more O atoms and has a OH end group as represented by an oligooxyethyleneglycol residue of 4 to 10 carbon atoms, preferably pentaoxyethyleneglycol.

$R_5$, $R_6$, $R_7$ and/or $R'_7$ may also be hydrocarbyl substituted by one or more functional groups, such as Cl, CHO, OH, SH, $NH_2$, $CONH_2$, COOH, COSH, $SO_3H$, $PO_3H_2$ or by a negatively charged group such as $COO^-$, $COS^-$, $SO_3^-$, or $PO_3^{2-}$. In one preferred embodiment, the functional group COOH, COSH, $SO_3H$, $PO_3H_2$, $COO^-$, $COS^-$, $SO_3^-$, or $PO_3^{2-}$ is an end functional group. In most preferred embodiments, the hydrocarbyl has 2 or 3 carbon atoms and an end group selected from $COO^-$, $PO_3^{2-}$, or, most preferably, $SO_3^-$.

In still a further embodiment, $R_5$, $R_6$, $R_7$ or $R'_7$ may be substituted by more than one OH and optionally $NH_2$ groups and may be the residue of a monoaccharide, e.g., glucosamine.

In another embodiment, $R_5$, $R_6$, $R_7$ or $R'_7$ may be the residue of an amino acid, a peptide or a protein. In one preferred embodiment, $R_5$ at any of the positions, but preferably at position $17^3$, is the residue of an amino acid, a peptide or a protein. The amino acid, peptide or protein may be the source of the negatively charged group if they contain a free terminal carboxyl group and/or a residue of an amino acid containing a non-terminal free carboxylic group, e.g. aspartic or glutamic acid.

In one embodiment, $R_5$, $R_6$, $R_7$ or $R'_7$ is the residue of an amino acid or peptide (oligopeptide or polypeptide) containing a hydroxy group, such as serine, threonine and tyrosine, or peptides containing them, or a derivative of said amino acid or peptide selected from esters such as alkyl, preferably methyl, esters, and N-protected derivatives wherein the N-protecting group is for example tert-butyloxy, carbobenzoxy or trityl, and said hydroxylated amino acid or peptide or derivative thereof is linked to the $COO^-$ group of the BChl derivative through its hydroxy group.

Examples of such amino acid derivatives are serine methyl ester, N-tert-butyloxycarbonyl-serine, N-trityl-serine methyl ester, tyrosine methyl ester, and N-tert-butoxy-tyrosine methyl ester, and an example of such a peptide is N-carbobenzoxy-seryl serine methyl ester, all of them prepared as described in the above-mentioned EP 0584552.

In another embodiment, $R_5$, $R_6$, $R_7$ and/or $R'_7$ is the residue of an amino acid or peptide (oligo or polypeptide) linked to —CO group through an amide bond (Y is NH).

In a further embodiment, $R_5$, $R_6$, $R_7$ or $R'_7$ is the residue of a cell-specific or tissue-specific ligand selected from peptides and proteins, which are exemplified by, but not limited to, hormone peptides, for example, melanocyte-stimulating hormones, e.g. α-MSH, and antibodies, e.g. immunoglobulins, and tumor-specific antibodies. The peptide or protein may be linked directly to the —CO group via an ester, thioester or amide bond, or it may be linked via an ester or amide bond to an end functional group of the $C_1$-$C_{25}$ hydrocarbyl radical selected from OH, COOH and $NH_2$.

As described in the above-mentioned EP 0584552, by conjugation of Bchl with different amino acids, and further conjugation of the Bchl amino acid conjugates with hormones, growth factors or derivatives thereof, or tumor-specific antibodies, or any other cell-specific ligands, suitable site-directed photosensitizers are obtained.

In one embodiment, the negatively charged group $COO^-$, $COS^-$, $SO_3^-$, or $PO_3^{2-}$ according to the invention originates from the functional group COOH, COSH, $SO_3H$, or $PO_3H_2$, respectively, of substituted hydrocarbyl chains of $R_5$, $R_6$, $R_7$ and/or $R'_7$. In another embodiment, the COOH, COSH, $COO^-$, and/or COS group is derived from $R_1$, $R_2$, and $R_4$ being OH or SH, $O^-R_8^+$ or $S^-R_8^+$, respectively, i.e., when a carboxylic or thiocarboxylic group or a carboxylate or thiocarboxylate anion is present at the position $13^1$, $15^1$ (m is 0), $15^2$ (m is 1), and/or $17^3$.

The cation $R_8^+$ may be a monovalent or divalent cation derived from an alkaline or alkaline earth metal such as $K^+$, $Na^+$, $Li^+$, $NH_4^+$, $Ca^+$, more preferably $K^+$; or $R_8^+$ is a cation derived from an amine.

In one preferred embodiment, the bacteriochlorophyll derivative of the invention has the formula I wherein:

M represents divalent Pd;

$R_1$ is —NH—$(CH_2)_n$—$SO_3^-R_8^+$, —NH—$(CH_2)_n$—$COO^-R_8^+$; —NH—$(CH_2)_n$—$PO_3^{2-}$ $(R_8^+)_2$;

$R_2$ is methoxy; and $R_3$ is —C(=O)—$CH_3$;

$R_8^+$ is a monovalent cation such as $K^+$, $Na^+$, $Li^+$, $NH_4^+$; and n is an integer from 1 to 10, preferably 2 or 3.

According to this embodiment, in the compound of formula I, $R_1$ is preferably a group —NH—$(CH_2)_n$—$SO_3^-R_8^+$, wherein n is 3 and $R_8^+$ is $K^+$.

In another preferred embodiment, the bacteriochlorophyll derivative of the invention has the formula II wherein:

M represents 2H, divalent Pd, Cu, or Zn or trivalent Mn;

$R_1$ is —$O^-R_8^+$, —NH—$(CH_2)_n$—$SO_3^-R_8^+$, —NH—$(CH_2)_n$—$COO^-R_8^+$; —NH—$(CH_2)_n$—$PO_3^{2-}$ $(R_8^+)_2$; or Y—$R_5$ wherein Y is O, S or NH and $R_5$ is the residue of an amino acid, a peptide or a protein;

$R_2$ is $C_1$-$C_6$ alkoxy such as methoxy, ethoxy, propoxy, butoxy, more preferably methoxy;

$R_3$ is —C(=O)—$CH_3$, —CH=N—$(CH_2)_n$—$SO_3^-R_8^+$; —CH=N—$(CH_2)_n$—$COO^-R_8^+$; —CH=N—$(CH_2)_n$—$PO_3^{2-}(R_8^+)_2$; —$CH_2$—NH—$(CH_2)_n$—$SO_3^-R_8^+$; —NH—$(CH_2)_n$—$COO^-R_8^+$; or —NH—$(CH_2)_n$—$PO_3^{2-}(R_8^+)_2$ $R_4$ is —NH—$(CH_2)_n$—$SO_3^-R_8^+$; —NH—$(CH_2)_n$—$COO^-R_8^+$; —NH—$(CH_2)_n$—$PO_3^{2-}(R_8^+)_2$;

$R_8^+$ is a monovalent cation such as $K^+$, $Na^+$, $Li^+$, $NH_4^+$, more preferably $K^+$; m is 1, and n is an integer from 1 to 10, preferably 2 or 3.

In a more preferred embodiment of the invention, the bacteriochlorophyll derivative has the formula II and M is Pd.

In another more preferred embodiment, the invention relates to a bacteriochlorophyll derivative of the formula II wherein:

M is Pd;

$R_1$ is —$O^-R_8^+$, —NH—$(CH_2)_n$—$SO_3^-R_8^+$, or Y—$R_5$ wherein Y is O, S or —NH and $R_5$ is the residue of a protein, preferably immunoglobulin;

$R_2$ is $C_1$-$C_6$ alkoxy such as methoxy, ethoxy, propoxy, butoxy, more preferably methoxy;

$R_3$ is —C(=O)—$CH_3$, —CH=N—$(CH_2)_n$—$SO_3^-R_8^+$; or —$CH_2^-NH^-(CH_2)_n$—$SO_3^-R_8^+$;

$R_4$ is —NH—$(CH_2)_n$—$SO_3^-R_8^+$; NH—$(CH_2)_n$—$COO^-R_8^+$; NH—$(CH_2)_n$—$PO_3^{2-}(R_8^+)_2$;

$R_8^+$ is a monovalent cation such as $K^+$, $Na^+$, $Li^+$, $NH_4^+$, more preferably $K^+$; and m is 1, and n is 2 or 3, more preferably 2.

An example of a bacteriochlorophyll derivative of the invention having a sole negatively charged group ($SO_3^-$) at position 17 is represented by the compound of Formula I identified in the List of Compounds hereinafter as compound 7.

Examples of bacteriochlorophyll derivatives of the invention having two negatively charged groups at positions 13 and 17 include the compounds of Formula II identified in the List of Compounds hereinafter as compounds 4, 5, 8, 10, 11, 12, 13, 14, 15. In a most preferred embodiment, the compound of the invention is compound 4.

Examples of bacteriochlorophyll derivatives of the invention having three negatively charged groups at positions 3, 13 and 17 include the compounds of formula II identified in the List of Compounds hereinafter as compounds 9 and 16. The compound 13 has one negatively charged group at position 13 and a —COOH group as part of the protein molecule at position $17^3$, and the compound 15 has one divalent negatively charged group at position 13 and a —$COO^-$ group at position $17^3$.

The compounds of the invention can be prepared, for example, by the methods as depicted in Scheme 1 herein. For the preparation of compounds wherein $R_5$ is the residue of an amino acid, peptide or protein, the methods described in the above-mentioned EP 0584552, particularly the catalytic condensation method, can be used as shown in Scheme 1 for the reaction with the aminosulfonic acids taurine and homotaurine.

Thus, a method for the preparation of compounds of formula II wherein $R_1$ is —$O^-R_8^+$; $R_2$ is —$OCH_3$; $R_3$ is acetyl; $R_4$ is a group —NH—$(CH_2)_n$—$SO_3^-R_8^+$; $R_8^+$ is a monovalent cation; m is 1 and n is 1 to 10, comprises: (i) reacting the corresponding M-bacteriopheophorbide of formula I wherein $R_1$ is OH with an aminosulfonic acid of the formula $H_2N$—$(CH_2)_n$—$SO_3H$ in a $R_8^+$-buffer; and (ii) isolating the desired compound of formula II.

For preparation of the compound 4, the method comprises reacting Pd-bacteriopheophorbide a 3 with taurine of the formula $H_2N$—$(CH_2)_2$—$SO_3H$ in a $K^+$-buffer, and isolating the desired compound.

For preparation of the compound 5, the method comprises reacting bacteriopheophorbide a 2 with taurine of the formula $H_2N$—$(CH_2)_2$—$SO_3H$ in a $K^+$-buffer, and isolating the desired compound.

For preparation of the Cu and Zn compounds 10, 11, the method comprises direct insertion of the central metal Cu or Zn atom by reacting the compound 5 with copper acetate or zinc acetate, respectively, while for preparation of the Mn compound 12, insertion of the central metal Mn atom is carried out by transmetalation by first reacting the compound 5 with cadmium acetate and then with manganese chloride.

A method for the preparation of compounds of formula II wherein $R_1$ is —$O^-R_8^+$; $R_2$ is —$OCH_3$; $R_3$ is acetyl; $R_4$ is a group —NH—$(CH_2)_n$—$COO^-R_8^+$; $R_8^+$ is a monovalent cation; m is 1 and n is 1 to 10, comprises: (i) reacting the corresponding M-bacteriopheophorbide of formula I wherein $R_1$ is OH with an aminocarboxylic acid of the formula $H_2N$—$(CH_2)_n$—COOH in a $R_8^+$-buffer; and (ii) isolating the desired compound of formula II.

Thus, for preparation of the compound 14, the method comprises reacting Pd-bacteriopheophorbide a 3 with β-alanine of the formula $H_2N$—$(CH_2)_2$—COOH in a $K^+$-buffer, and isolating the desired compound.

A method for the preparation of compounds of formula II wherein $R_1$ is —$O^-R_8^+$; $R_2$ is —$OCH_3$; $R_3$ is acetyl; $R_4$ is a group —NH—$(CH_2)_n$—$PO_3^{2-}$ $(R_8^+)_2$; $R_8^+$ is a monovalent cation; m is 1 and n is 1 to 10, comprises: (i) reacting the corresponding M-bacterio-pheophorbide of formula I wherein $R_1$ is OH with an aminophosphonic acid of the formula $H_2N$—$(CH_2)_n$—$PO_3H_2$ in a $R_8^+$-buffer; and (ii) isolating the desired compound of formula II.

Thus, for preparation of the compound 15, the method comprises reacting Pd-bacteriopheophorbide a 3 with 3-amino-1-propanephosphonic acid of the formula $H_2N$—$(CH_2)_3$—$PO_3H_2$ in a $K^+$-buffer, and isolating the desired compound.

For the preparation of compounds having the same negatively charged groups at positions 13 and 17, the corresponding M-bacteriopheophorbide can be reacted with an excess of the reagent such as aminosulfonic, aminocarboxylic or aminophosphonic acid as described above, and isolation of the desired 13,17-disubstituted derivative of formula II, or a different route can be followed as depicted in Scheme 1 herein and described below.

Thus, a method for the preparation of compounds of formula II wherein $R_1$ and $R_4$ are each a group —NH—$(CH_2)_n$—$SO_3^-R_8^+$; $R_2$ is —$OCH_3$; $R_3$ is acetyl; $R_8^+$ is a monovalent cation; m is 1 and n is 1 to 10, comprises: (i) coupling the corresponding M-bacteriopheophorbide of formula I wherein $R_1$ is OH with N-hydroxy-sulfosuccinimide (sulfo NHS) in the presence of 1-ethyl-3-(3-dimethylaminopropyl)-carbodiimide (EDC); (ii) reacting the resulting M-bacteriopheophorbide-$17^3$-N-hydroxysulfosuccinimide ester with an excess of an aminosulfonic acid of the formula $H_2N$—$(CH_2)_n$—$SO_3H$ in a $R_8^+$-buffer, thus obtaining a compound of formula I having a sole negatively charged group at position 17; (iii) reacting this product with an excess of $H_2N$—$(CH_2)_n$—$SO_3H$ in a $R_8^+$-buffer; and isolating the desired compound of formula II.

For the preparation of the compound 8, the reaction is carried out with an excess of homotaurine of the formula $H_2N$—$(CH_2)_3$—$SO_3H$.

When the aminosulfonic acid is replaced by aminocarboxylic or aminophosphonic acid, the corresponding carboxylate and phosphonate derivatives are obtained.

The compounds of the invention, also referred herein sometimes by the term "pigments", present sufficient high polarity to be water soluble and injected in aqueous solutions with no added surfactants. In one embodiment, for the preferred sulfonated-Pd-Bchl compound 4 also biodistribution and pharmacokinetics are shown and, based thereon, it is assumed that this and the other derivatives of the invention remain in the circulation, and for a very short time. Therefore they are good sensitizers for vascular-targeting PDT. Treatment of M2R melanotic melanoma and HT-29 human colon carcinoma xenografts in mice shown herein, demonstrate the selective effect of the pigment on the tumor vasculature. The suggested protocol with sulfonated-Pd-Bchl 4 considered the short clearance time of the drug. On the ground of their selective effect on the tumor vasculature, these compounds can be used for tumor as well as age-related macular degeneration and other tissues abnormalities that depend on neovascularization.

Thus, in another aspect, the present invention provides a pharmaceutical composition comprising a bacteriochlorophyll derivative of the invention and a pharmaceutically acceptable carrier.

In a preferred embodiment, the pharmaceutical composition comprises a bacteriochlorophyll derivative of formula I or II herein, more preferably a sulfonated derivative of formula II, most preferably the compound 4.

The anionic bacteriochlorophyll derivatives of the present invention are formulated into final pharmaceutical compositions for administration to the patient or applied to an in vitro target using techniques well-known in the art, for example, as summarized in Remington's Pharmaceutical Sciences, Mack Publishing Co., Easton, Penna., latest edition. The compositions can be administered systemically, in particular by injection, or can be used topically.

The anionic Bchl compounds of the invention have similar optical absorption and photophysical characteristics as the respective non-anionic Bchls and, therefore, once residing within the treated tissue, they are expected to be efficient photodynamic agents. They can thus be useful as photosensitizers as therapeutic and diagnostic agents, for example for treatment of several cancer types such as, but not limited to, melanoma, prostate, brain, colon, ovarian, breast, skin, lung, esophagus and bladder cancers and other hormone-sensitive tumors, as well as for treatment of age-related macular degeneration, and for killing cells, viruses, fungi and bacteria in samples and living tissues as well known in the art of PDT and other photosensitizer applications.

The new water-soluble Bchl derivatives of the invention are useful, for example, in sensitizing neoplastic cells or other abnormal tissue to destruction by irradiation either in vivo or ex vivo using light of appropriate wavelength. It is believed that the energy of photoactivation is transferred to endogenous oxygen to convert it to singlet oxygen, and/or other reactive oxygen species (ROS) such as superoxide and hydroxyl radicals, which are considered to be responsible for the cytotoxic effect. In addition, the photoactivated forms of the Bchls fluoresce, which fluorescence can aid in localizing tumors or other sites to which the Bchl derivative is administered.

Examples of indications, known in the art, that can be treated with the bacteriochlorophyll derivatives of the present invention, include destruction of tumor tissue in solid tumors and dissolution of plaques in blood vessels (see, e.g., U.S. Pat. No. 4,512,762). Particularly, these derivatives are suitable for vascular-targeted PDT because of their minimal retention in the circulation and because they are taken-up only minimally by non-circulating tissues such as skin and muscle. Thus, these compounds enable reactive oxygen species (ROS) generation limited to the interior vessels upon excitation and, thereby, cause selective response of abnormal vessels such as those present in tumors and age-related macular degeneration. In addition, the bacteriochlorophyll derivatives are useful for selective destruction in treatment of topical conditions such as acne, athlete's foot, warts, papilloma, and psoriasis, for treatment of benign prostate hypertrophy and for sterilization of biological products such as blood for transfusion, by destruction of infectious agents.

The pharmaceutical compositions of the invention will be administered to the patient by standard procedures used in PDT. The amount of the anionic Bchl derivative of the invention to be administered to an individual in need and the route of administration will be established according to the experience accumulated with other porphyrins used in PDT, and will vary depending on the choice of the derivative used as active ingredient, the condition, e.g. the kind of tumor, to be treated, the stage of the disease, age and health conditions of the patient, and the judgement of the physician, but will be much lower than currently used dosage of Photofrin II of about 20-40 mg HPD/kg body weight. The preferable routes of administration are intravenous or direct injection into the solid tumor of the aqueous solution of the active compound comprising conventional pharmaceutically acceptable carriers and additives, and topical treatment of skin tumors with suitable topical compositions.

The wavelength of irradiating light is preferably chosen to match the maximum absorbance of the bacteriochlorophyll photosensitizer. The suitable wavelength for any of the compounds can readily be determined from its absorption spectrum.

In addition to in vivo use, the anionic Bchl derivatives of the invention can be used in the treatment of materials in vitro to kill harmful viruses or infectious agents, such as harmful bacteria. For example, blood and blood plasma to be used for future transfusion can be treated with a Bchl of the invention and irradiated to effect sterilization.

The conjugation of proteins, e.g., hormones, growth factors or their derivatives, antibodies, peptides that bind specifically to target cells receptors, and of cell nutrients, e.g. tyrosine, to the Bchl moiety is meant to increase their retention in tumor and treated sites. Increasing the red shift allows for a greater depth of penetration, while keeping the ubiquity of the natural system. Replacement of the Mg by other metals is meant to optimize the intrinsic and metabolic stability of the Bchl moiety and its intersystem crossing to the excited triplet state, and also opens the possibility for new diagnostic procedures.

Tumor-specific antibodies and peptides that have high affinity to neoendothelial cells will preferentially target the Bchl moieties to the tumor or treated site, while hormones and cell nutrients may also be taken up by the normal non-transformed counterparts. However, the cells selected as targets to hormones and cell nutrients, such as melanocytes and neoendothelial cells are scattered among other cells under normal conditions and when transformed into malignant cells, cluster into solid tumors. As a result, the concentration of the photosensitizer in the vascular and/or cellular compartments of the malignant tissue is expected to increase dramatically relative to its concentration in the normal tissue, where cells are more dispersed, assuring amplification of the PDT effect in the tumor site. This enables effective use of light doses, lower than the damaging threshold of the normal tissue, thus reducing the need for spatially well-defined irradiation. In addition, having very strong fluorescence, the site-directed Bchl can be used for fluorescence labeling of the tumor site(s) or other targets.

In one most preferred embodiment of the present invention, the target for treatment with the sensitizers of the invention are abnormal blood vessels, particularly blood vessels of solid tumors and age-related macular degeneration, due to the inherent difference of sensitivity of normal and abnormal blood vessels to the suggested PDT protocols described herein.

The invention further relates to a method of photodynamic therapy, which comprises administering to an individual in need an effective amount of a Bchl derivative of the invention, followed by local irradiation.

In one embodiment, the PDT method of the invention is used for treatment of cancer and comprises administering to a patient afflicted with a solid tumor cancer a therapeutically effective amount of a Bchl derivative according to the invention, and then irradiating the tumor site with strong light sources at 670-780 nm The Bchl derivatives of the invention are also useful for photodestruction of normal or malignant animal cells as well as of microorganisms in culture, enabling selective photodestruction of certain types of cells in culture or infective agents; for targeting of the porphyrin moiety to selected cells by attachment to specific polypeptides, such as hormones or other receptor ligands, to cell- or tissue-specific antibodies or to other ligands, e.g., lectins; for fluorescent labeling/tagging of molecules for analytical purposes in laboratory, diagnostic and industrial applications; and for fluorescent labeling of animal cells or microorganisms or particles for laboratory, diagnostic or industrial applications. They can replace several of the currently used fluorescence tags, such as fluorescein isothiocyanate (FITC) or phycoerythrine, due to their superior extinction coefficients and higher fluorescence yield.

For diagnostic purposes, the Bchl derivatives of the invention may be used alone or may be labeled with a radioisotope or other detecting means as known in the art. For example, the Bchl derivative can be radioactively-labeled by standard procedures, e.g., with $^{67}$Ga, $^{111}$In, $^{201}$Tl, $^{99}$mTc, and the radioactive diagnostic agent is administered to the patient, preferably by intravenous injection. After some hours, the locus of the cancer may be imaged by standard procedures.

The invention further provides the use of the Bchl derivatives of the invention for ex-vivo or in vitro killing of cells or infectious agents such as bacteria, viruses, parasites and fungi in a biological product, e.g. blood, which comprises treating the infected sample with the compound of the invention followed by illumination of the sample.

The invention will now be illustrated by the following non-limitative Examples.

EXAMPLES

For convenience and better understanding, the section of the Examples is divided into two subsections: (I) the Chemical Section, describing the synthesis of the water-soluble derivatives and intermediates 4-16, and (II) the Biological Section, describing the biological activity of the new Bchl derivatives.

I Chemical Section

In the Examples herein, the derivatives of the invention (4-5, 7-9, and 10-16) and the intermediates (1-3, and 6) will be presented by their respective Arabic numbers in bold and underlined according to the following List of Compounds. The corresponding formulas appear in the Scheme at the end of the specification, just before the claims.

LIST OF COMPOUNDS

1. Bacteriochlorophyll a (Bchl a)
2. Bacteriopheophorbide a (Bpheid a)
3. Pd-Bacteriopheophorbide a (Pd-Bpheid a)
4. Palladium $3^1$-oxo-15-methoxycarbonylmethyl-Rhodobacteriochlorin $13^1$-(2-sulfo-ethyl)amide dipotassium salt [Example 1]
5. $3^1$-oxo-15-methoxycarbonylmethyl-Rhodobacteriochlorin $13^1$-(2-sulfoethyl)amide dipotassium salt [Example 2]
6. Palladium bacteriopheophorbide a $17^3$—(3-sulfo-1-oxysuccinimide) ester sodium salt [Example 6]
7. Palladium Bacteriopheophorbide a $17^3$-(3-sulfopropyl) amide potassium salt [Example 7]
8. Palladium $3^1$-oxo-15-methoxycarbonylmethyl-Rhodobacteriochlorin $13^1$,$17^3$-di(3-sulfopropyl)amide dipotassium salt [Example 8]
9. Palladium $3^1$-(3-sulfopropylimino)-15-methoxycarbonylmethyl-Rhodobacteriochlorin $13^1$,$17^3$-di(3-sulfopropyl) amide tripotassium salt [Example 9]
10. Copper(II) $3^1$-oxo-15-methoxycarbonylmethyl-Rhodobacteriochlorin $13^1$-(2-sulfoethyl)amide dipotassium salt [Example 3]
11. Zinc $3^1$-oxo-15-methoxycarbonylmethyl-Rhodobacteriochlorin $13^1$-(2-sulfoethyl) amide dipotassium salt [Example 4]
12. Manganese(III) $3^1$-oxo-15-methoxycarbonylmethyl-Rhodobacteriochlorin $13^1$-(2-sulfoethyl)amide dipotassium salt [Example 5]
13. Palladium $3^1$-oxo-[5-methoxycarbonylmethyl-Rhodobacteriochlorin $13^1$-(2-sulfoethyl)amide, $17^3$-(N-immunoglobulin G)amide potassium salt] [Example 10]
14. Palladium $3^1$-oxo-15-methoxycarbonylmethyl-Rhodobacteriochlorin $13^1$-(2-carboxyethyl)amide dipotassium salt [Example 11]
15. Palladium $3^1$-oxo-15-methoxycarbonylmethyl-Rhodobacteriochlorin $13^1$-(3-phosphopropyl)amide tripotassium salt [Example 12]
16. Palladium $3^1$-(3-sulfopropylamino)-15-methoxycarbonylmethyl-Rhodobacteriochlorin $13^1$,$17^3$-di(3-sulfopropyl) amide tripotassium salt [Example 13]

Materials and Methods (i) Bchl a (1) was extracted and purified from lyophilized cells of *Rhodovolum Sulfidophilum* as previously described (WO 00/33833).

(ii) Palladium bacteriopheophorbide (Pd-Bpheid, 3) was either prepared as previously described (WO 00/33833) or it was obtained from Steba Biotech Ltd. through Negma-Lerads, France.

(iii) 3-Amino-1-propane sulfonic acid (homotaurine) and 3-amino-1-propane phosphonic acid were purchased from Aldrich (USA), and 2-aminoethane sulfonic acid (taurine) and 3-aminopropionic acid (β-alanine) were purchased from Sigma (USA), N-hydroxy-sulfosuccinimide (sulfo-NHS) was purchased from Pierce (USA), 1-(3-dimethylaminopropyl)-3-ethylcarbodiimide (EDC) was purchased from Fluka (Switzerland).

(iv) Chemicals and solvents of analytical grade were generally used except when performing HPLC, where HPLC-grade solvents were applied.

(v) TLC: silica plates (Kieselgel-60, Merck, Germany); chloroform-methanol (4:1, v/v).

(vi) $^1$H Nuclear magnetic resonance (NMR) spectra were recorded on Avance DPX 250 instrument (Bruker, France) and reported in ppm (δ) downfield from tetramethylsilane with residual solvent peaks as the internal standards.

(vii) The extinction coefficients of the Pd-derivatives were determined by correlating the Pd concentration (using flame photometry with $PdCl_2$ as a standard) with the optical density of the examined solution at the particular wavelength.

(viii) Electrospray ionization mass spectra (ESI-MS) were recorded on a platform LCZ spectrometer (Micromass, England).

(ix) Inductively-Coupled Plasma Mass Spectrometry (ICP-MS) was performed for determination of Pd concentrations using an ELAN-6000 instrument (Perkin Elmer, Conn.).

(x) Optical absorption of the different complexes was recorded with Genesis-2 (Milton Roy, England) and V-570 (JASCO, Japan) spectrophotometers.

(xi) HPLC was performed using an LC-900 instrument (JASCO, Japan) equipped with a UV-915 diode-array detector.

CHEMICAL EXAMPLES

Example 1

Palladium 3$^1$-oxo-15-methoxycarbonylmethyl-Rhodobacteriochlorin 13$^1$-(2-sulfoethyl)amide dipotassium salt (Compound 4)

Nine hundred and thirty five (935) mg of Pd-Bpheid (I) were dissolved in a 1 L round bottom flask with 120 ml of DMSO while stirring under Argon (bubbled in the solution). Taurine (1288 mg) was dissolved in 40 ml of 1M $K_2HPO_4$ buffer, and the pH of the solution was adjusted to 8.2 (with HCl). This aqueous solution was added into the DMSO solution while stirring, and the Argon was bubbled in the solution for another 20 minutes. Then the reaction mixture was evaporated at 30° C. for 3.5 hours under ~2 mbar and then for another 2 hours at 37° C. to a complete dryness. The dry solids were dissolved in 300 ml of MeOH and the colored solution was filtered through cotton wool to get rid of buffer salts and taurine excess.

The progress of the reaction was determined by TLC($R_f$ of unreacted Pd-Bpheid is 0.8-0.85 and of the reaction (aminolysis) product is 0.08-0.1) and by following the optical absorption spectrum of the reaction mixture after liophylization and resolubilization in MeOH. The absorption spectrum was characterized by a $Q_y$ transition shift from 756 nm (for Pd-Bpheid) to 747 nm (for the product 4) and by $Q_x$ shift from 534 nm of Pd-Bpheid to 519 nm (of the product 4). The MeOH was evaporated and the product 4 was purified by HPLC with ODS-A 250×20 S10P μm column (YMC, Japan). Solvent A: 95% 0.005 M phosphate buffer, pH 8.0 and 5% MeOH. Solvent B: 100% MeOH. The dry solid was dissolved in 42 ml of distilled water and injected in portions of 1.5 ml each.

The elution profile is described in Table 1. The product 4 (Scheme 1, see below) was eluted and collected at ~9-11 minutes. The main impurities, collected after at 4-7 min (ca 5-10%), corresponded to byproduct(s) with the proposed structure 7. Peaks at 22-25 min (ca 2-5%) possibly corresponded to the iso-form of the main product 4 and untreated Pd-Bpheid residues.

TABLE 1

Gradient profile of purification of compound 4

| Time (min) | Flow (ml/min) | A % | B % |
|---|---|---|---|
| 0 | 12 | 55 | 45 |
| 14 | 12 | 30 | 70 |
| 14.1 | 6 | 30 | 70 |
| 16 | 6 | 0 | 100 |
| 18 | 6 | 0 | 100 |
| 24 | 6 | 55 | 45 |
| 29 | 6 | 55 | 45 |
| 30 | 0.5 | 55 | 45 |

The solvent (aqueous methanol) was evaporated under reduced pressure. Then, the purified product 4] was re-dissolved in ~150 ml MeOH and filtered through cotton wool. The solvent was evaporated again and the solid pigment 4 was stored under Ar in the dark at ~20° C. The reaction yield: ~90% (by weight, relative to 3).

Figure 4:
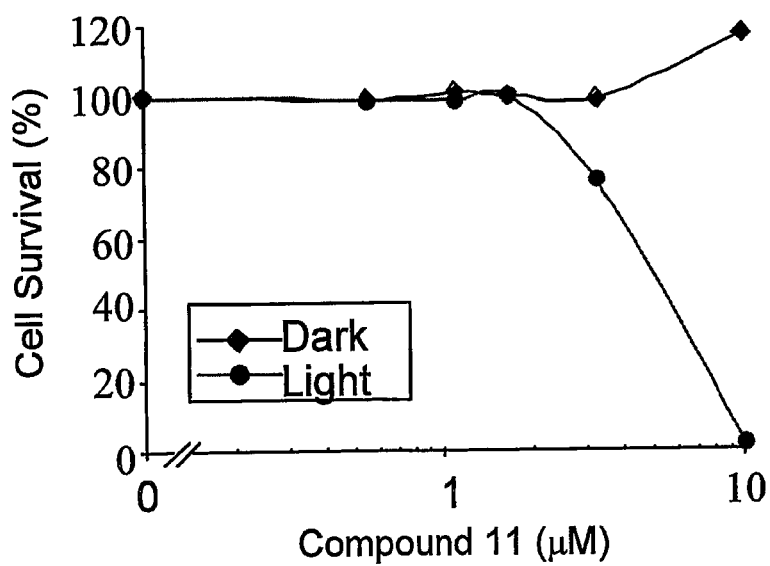
FIG. 4 is a graph showing the phototoxicity of the sulfonated compound 11 on M2R mouse melanoma cells. Cells were incubated with increasing concentrations of compound 11 for 4 hours, washed and illuminated (circles) or kept in the dark (dark control, diamonds). Points are average of triplicates.

The structure of product 4 was confirmed by electrospray mass spectroscopy. (ESI-MS, negative mode, FIG. 2), (peaks at 875 (M$^-$—K—H), 859 (M$^-$-2K—H+Na), 837 (M$^-$-2K), 805 (M2K—H—OMe), 719) and $^1$H-NMR spectrum (FIG. 4 in MeOH-$d_4$). Table 4 provides the shifts (in ppm units) of the major NMR peaks.

Optical absorption (UV-VIS) spectrum (MeOH): λ, 747 (1.00), 516 (0.13), 384 (0.41), 330 (0.50); $\epsilon_{747}$ (MeOH) is $1.2 \times 10^5$ mol$^{-1}$ cm$^{-1}$.

NMR (MeOH-$d_4$): 9.38 (5-H, s), 8.78 (10-H, s), 8.59 (20-H, s), 5.31 and 4.95 (15$^1$-CH$_2$, dd), 4.2-4.4 (7,8,17,18-H, m), 3.88 (15$^3$-Me, s), 3.52 (2$^1$-Me, s), 3.19 (12$^1$-Me, s), 3.09 (3$^2$-Me, s), 1.92-2.41, 1.60-1.75 (17$^1$, 17$^2$-CH$_2$, m), 2.19 (8$^1$-CH$_2$, m), 1.93 (7$^1$-Me, d), 1.61 (18$^1$-Me, d), 1.09 (8$^2$-Me, t), 3.62, 3.05 (CH$_2$'s of taurine).

Octanol/water partition ratio is 40:60.

Example 2

Preparation of 3$^1$-oxo-15-methoxycarbonylmethyl-Rhodobacteriochlorin 13$^1$-(2-sulfoethyl)amide dipotassium salt (Compound 5)

One hundred and sixty (160) mg of taurine were dissolved in 5 ml of 1M $K_2HPO_4$ buffer, and the pH of the solution was adjusted to 8.2. This solution was added to 120 mg of compound 2 dissolved in 15 ml of DMSO, and the reaction and following purification were analogous to those described in previous Example.

Absorption spectrum (MeOH): λ, 750 (1.00), 519 (0.30), 354 (1.18) nm.

ESI-MS (−): 734 (M$^-$-2K).

NMR (MeOH-$d_4$): 9.31 (5-H, s), 8.88 (10-H, s), 8.69 (20-H, s), 5.45 and 5.25 (15$^1$-CH$_2$, dd), 4.35 (7,18-H, m), 4.06

(8,17-H, m), 4.20 and 3.61 (2-$CH_2$, m of taurine), 3.83 ($15^3$-Me, s), 3.63 ($2^1$-Me, s), 3.52 (3-$CH_2$, m of taurine), 3.33 (12'-Me, s), 3.23 ($3^2$-Me, s), 2.47 and 2.16 (17'-$CH_2$, m), 2.32 and 2.16 ($8^1$-$CH_2$, m), 2.12 and 1.65 ($17^2$-$CH_2$, m), 1.91 ($7^1$-Me, d), 1.66 (18'-Me, d), 1.07 ($8^2$-Me, t).

Octanol/water partition ratio is 60:40.

Example 3

Preparation of copper(II) $3^1$-oxo-15-methoxycarbonylmethyl-Rhodobacteriochlorin 13'-(2-sulfoethyl)amide dipotassium salt (Compound 10)

Fifty (50) mg of compound 5 of Example 2 and 35 mg of copper (II) acetate were dissolved in 40 ml of methanol, and argon was bubbled into solution for 10 minutes. Then 500 mg of palmitoyl ascorbate was added, and the solution was stirred for 30 min. The absorption spectrum was characterized by a $Q_y$ transition shift from 750 nm (for 5) to 768 nm (for the product L)) and by $Q_x$ shift from 519 nm of 5 to 537 nm (of the product 10). Then the reaction mixture was evaporated, re-dissolved in acetone and filtered through cotton wool to get rid of acetate salt excess. The acetone was evaporated and the product was additionally purified by HPLC at the conditions mentioned above with the elution profile, described in Table 2.

The solvent (aqueous methanol) was evaporated under reduced pressure. Then, the purified pigment 10 was re-dissolved in methanol and filtered through cotton wool. The solvent was evaporated again and the solid pigment 10 was stored under Ar in the dark at −20° C. Reaction yield: ~90%.

TABLE 2

Gradient profile of purification of compound 10

| Time (min) | Flow (ml/min) | A % | B % |
|---|---|---|---|
| 0 | 12 | 58 | 42 |
| 14 | 12 | 45 | 55 |
| 14.1 | 6 | 45 | 55 |
| 16 | 6 | 0 | 100 |
| 18 | 6 | 0 | 100 |
| 24 | 6 | 58 | 42 |
| 29 | 6 | 58 | 42 |
| 30 | 0.5 | 58 | 42 |

Absorption spectrum (MeOH): λ, 768 (1.00), 537 (0.22), 387 (0.71) and 342 (0.79) nm.

ESI-MS (−): 795 ($M^-$-2K).

Octanol/water partition ratio is 40:60.

Example 4

Preparation of zinc $3^1$-oxo-15-methoxycarbonylmethyl-Rhodobacteriochlorin 13'-(2-sulfoethyl)amide dipotassium salt (Compound 11)

Zn insertion into compound 5 was carried out with Zn acetate in acetic acid as previously described (U.S. Pat. No. 5,726,169). Final purification was carried out by HPLC in the same conditions as for compound 5 in Example 2 above.

Absorption spectrum (MeOH): λ, 762 (1.00), 558 (0.26), 390 (0.62) and 355 (0.84) nm.

Octanol/water partition ratio is 50:50.

Example 5

Preparation of manganese(III) $3^1$-oxo-15-methoxycarbonylmethyl-Rhodobacteriochlorin 13'-(2-sulfoethyl)amide dipotassium salt (Compound 12)

Mn insertion into compound 5 was carried out with Zn acetate in acetic acid as previously described (WO 97/19081; U.S. Pat. No. 6,333,319) with some modifications. Thus, fifty (50) mg of compound 5 in 10 ml of DMF were stirred with 220 mg of cadmium acetate and heated under argon atmosphere at 110° C. about 15 min (Cd-complex formation is monitored by shifting $Q_x$ transition absorption band from 519 to 585 nm in acetone). Then the reaction mixture was cooled and evaporated. The dry residue was re-dissolved in 15 ml of acetone and stirred with manganese (II) chloride to form the Mn(III)-product 12. The product formation is monitored by shifting $Q_x$ transition band from 585 to 600 nm and $Q_y$ transition band from 768 to 828 nm in acetone. The acetone was evaporated and the product 12 was additionally purified by HPLC in the conditions mentioned in Example 2 above with the elution profile described in Table 3 below where the] solvent system consists of: A—5% aqueous methanol, B—methanol.

TABLE 3

Gradient profile of purification of compound 12

| Time (min) | Flow (ml/min) | A % | B % |
|---|---|---|---|
| 0 | 8 | 95 | 5 |
| 14 | 8 | 55 | 45 |
| 14.1 | 8 | 55 | 45 |
| 16 | 8 | 0 | 100 |
| 18 | 8 | 0 | 100 |
| 24 | 8 | 95 | 5 |
| 29 | 8 | 95 | 5 |
| 30 | 0.5 | 95 | 5 |

The solvent (aqueous methanol) was evaporated under reduced pressure and the solid pigment 12 was stored under Ar in the dark at −20° C.

Absorption spectrum (MeOH): λ, 828 (1.00), 588 (0.32) and 372 (0.80) nm

Octanol/water partition ratio is 5:95.

Example 6

Preparation of palladium bacteriopheophorbide a $17^3$-(3-sulfo-1-oxy-succinimide)ester sodium salt (Compound 6)

Fifty (50) mg of Pd-Bpheid (compound 2), 80 mg of N-hydroxy-sulfosuccinimide (sulfoNHS) and 65 mg of 1-(3-dimethylaminopropyl)-3-ethylcarbodiimide (EDC) were mixed in 7 ml of dry DMSO for overnight at room temperature. Then the solvent was evacuated under reduced pressure. The dry residue was re-dissolved in chloroform (ca. 50 ml), filtered from insoluble material, and evaporated. The conversion was ab. 95% (TLC). The product 6 was used later on without further chromatographic purification. ESI-MS (−): 890 ($M^-$-Na).

NMR (CDCl$_3$): 9.19 (5-H, s), 8.49 (10-H, s), 8.46 (20-H, s), 5.82 ($13^2$-H, s), 4.04-4.38 (7,8,17,18-H, m), 3.85 ($13^4$-Me, s), 3.47 ($2^1$-Me, s), 3.37 (12$^1$-Me, s), 3.09 ($3^2$-Me, s), 1.77 ($7^1$-Me, d), 1.70 ($18^1$-Me, d), 1.10 ($8^2$-Me, t), 4.05 ($CH_2$ of sNHS), 3.45 (CH of s NHS).

Example 7

Preparation of palladium bacteriopheophorbide a 17³-(3-sulfopropyl) amide potassium salt (Compound 2)

Ten (10) mg of compound 6 in 1 ml of DMSO was mixed with 20 mg of homotaurine (3-amino-1-propane-sulfonic acid) in 1 ml of 0.1 M K-phosphate buffer, pH 8.0 for overnight. Then the reaction mixture was partitioned in chloroform/water. The organic layer was dried over anhydrous sodium sulfate and evaporated. The dry residue was re-dissolved in chloroform-methanol (19:1) and applied to a chromatographic column with silica. The product 7 was obtained with chloroform-methanol (4:1) elution. The yield was about 80-90%.

ESI-MS (−): 834 (M-K) m/z.

NMR (MeOH-$d_4$): 9.16 (5-H, s), 8.71 (10-H, s), 8.60 (20-H, s), 6.05 ($13^2$-H, s), 4.51, 4.39, 4.11, 3.98 (7,8,17,18-H, all m), 3.92 ($13^4$-Me, s), 3.48 ($2^1$-Me, s), 3.36 ($12^1$-Me, s), 3.09 ($3^2$-Me, s), 2.02-2.42 ($17^1$ and $17^2$-$CH_2$, m), 2.15 ($8^1$-$CH_2$, q), 1.81 ($7^1$-Me, d), 1.72 ($18^1$-Me, d), 1.05 ($8^2$-Me, t), 3.04, 2.68, and 2.32 ($CH_2$'s of homotaurine, m).

Example 8

Preparation of palladium 3¹-oxo-15-methoxycarbonylmethyl-Rhodobacteriochlorin 13¹,17³-di(3-sulfopropyl)amide dipotassium salt (Compound 8)

Ten (10) mg of compound 6 or 7 were dissolved in 3 ml of DMSO, mixed with 100 mg of homotaurine in 1 ml of 0.5 M K-phosphate buffer, pH 8.2, and incubated overnight at room temperature. The solvent was then evacuated under reduced pressure as described above, and the product 8 was purified on HPLC. Yield: 83%.

Absorption spectrum (MeOH): 747 (1.00), 516 (0.13), 384 (0.41), 330 (0.50), $\epsilon_{747}$=1.3×10⁵ $mol^{-1}$ $cm^{-1}$.

ESI-MS (−): 1011 (M⁻-K), 994 (M⁻-2K⁺ Na), 972 (M⁻-2K), 775 (M⁻-2K—$CO_2$Me-homotaurine $NHCH_2CH_2CH_2SO_3$), 486 ([M-2K]/2)

NMR (MeOH-$d_4$): 9.35 (5-H, s), 8.75 (10-H, s), 8.60 (20-H, s), 5.28 and 4.98 ($15^1$-$CH_2$, dd), 4.38, 4.32, 4.22, 4.15 (7,8,17,18-H, all m), 3.85 (15-Me, s), 3.51 ($2^1$-Me, s), 3.18 ($12'$-Me, s), 3.10 ($3^2$-Me, s 2.12-2.41 ($17'$-$CH_2$, m), 2.15-2.34 ($8^1$-$CH_2$, m), 1.76-2.02 ($17^2$-$CH_2$, m), 1.89 ($7^1$-Me, d), 1.61 ($18'$-Me, d), 1.07 ($8^2$-Me, t). 3.82, 3.70, 3.20, 3.10, 2.78, 2.32, 1.90 ($CH_2$'s of homotaurine at C-13' and C-17³)

Example 9

Palladium 3¹-(3-sulfopropylimino)-15-methoxycarbonylmethyl-Rhodo-bacteriochlorin 13',17³-di(3-sulfopropyl)amide tripotassium salt (Compound 9)

Compound 9 was obtained from HPLC as a minor product during synthesis of 8.

Absorption spectrum (MeOH): 729 (1.00), 502 (0.10), 380 (0.69), 328 (0.57).

ESI-MS (30.4.2000): 1171 (M-K⁺ H), 1153 (M⁻-2K–H+ Na), 1131 (M-2K), 566 ([M-K]/2), 364 ([M-3K]/3).

NMR (MeOH-$d_4$): 8.71 (1H), 8.63 (1.5H), 8.23 (0.5H) (5-, 10- and 20-H, all-m), 5.30 and 4.88 ($15^1$-$CH_2$, dd), 4.43 and 4.25 (7,8,17,18-H, m), 3.85 ($15^1$-Me, s), 3.31 ($2^1$-Me, s), 3.22 ($12'$-Me, s), 3.17 ($3^2$-Me, m), 1.89-2.44 ($17'$ and $17^2$-$CH_2$, m), 2.25 ($8^1$-$CH_2$, m), 1.91 ($7^1$-Me, s), 1.64 ($18'$-Me, s), 1.08 ($8^2$-Me, t), 4.12, 3.56, 3.22, 3.16, 2.80 and 2.68 ($CH_2$'s of homotaurine).

Example 10

Palladium 3¹-oxo-15-methoxycarbonylmethyl-Rhodobacteriochlorin 13'-(2-sulfoethyl)amide, 17³-(N-immunoglobulin G)amide potassium salt (Compound 13)

Ten (10) mg of compound 4 were reacted with 20 mg of sulfo-NHS and 15 mg of EDC in 1 ml of dry DMSO for 1 hour at room temperature, then rabbit IgG (0.6 mg) in PBS (2.5 ml) was added, and the mixture was further incubated overnight at room temperature. The mixture was evaporated to dryness, then re-dissolved in 1 ml of PBS and loaded on Sephadex G-25 column equilibrated with PBS. A colored band was eluted with 4-5 ml of PBS. The pigment/protein ratio in the obtained conjugate 13 was determined by optical density at 753 and 280 nm, respectively, and varied between 0.5/1 to 1/1 of pigment 13/protein.

Example 11

Preparation of palladium 3'-oxo-15-methoxycarbonylmethyl-Rhodobacteriochlorin 13'-(2-carboxyethyl) amide dipotassium salt (Compound 14)

The preparation and purification of the title compound 14 were carried out as described in Example 2, by reaction of compound 2 with 3-aminopropionic acid (-alanine) (150 mg) instead of taurine. Yield: 85%.

Example 12

Preparation of palladium 3¹-oxo-15-methoxycarbonylmethyl-Rhodobacteriochlorin 13'-(3-phosphopropyl)amide tripotassium salt (Compound 15)

The preparation and purification of the title compound 15 were carried out as described in Example 2, by reaction of compound 2 with 3-amino-1-propanephosphonic acid (180 mg) instead of taurine. Yield: 68%.

Example 13

Palladium 3¹-(3-sulfopropylamino)-15-methoxycarbonylmethyl-Rhodobacteriochlorin 13',17³-di(3-sulfopropyl)amide tripotassium salt (Compound 16)

For reduction of the imine group in 3¹-(3-sulfopropylimino) to the correspondent 3¹-(3-sulfopropylamino) group, compound 9 (8 mg) was reacted by stiffing with sodium cyanoborohydride (15 mg) in 5 ml of methanol overnight at room temperature. Then the reaction mixture was treated with 0.05 M HCl (5 ml), neutralized with 0.01 M KOH, and evaporated. The title product 16 was purified using HPLC conditions as described in Example 2. Yield: 80-90%.

II Biological Section
Materials and Methods
In Vitro Studies
(i) Cell Culture.

M2R mouse melanoma, H5V mouse endothelial and C6 rat glioma cells were cultured as monolayers in Dulbecco's modified Eagle's medium (DMEM)/F12 containing 25 mM HEPES, pH 7.4, 10% fetal bovine serum (FBS), glutamine (2 mM), penicillin (0.06 mg/ml), and streptomycin (0.1 mg/ml) (hereinafter referred to as the "Culture Medium"). Cells were grown at 37° C. in an 8% $CO_2$-humidified atmosphere.

(ii) Phototoxicity Assay.

To determine the photodynamic efficacy, cells were preincubated with increasing concentrations of the pigments in the dark for the times and conditions as indicated for the individual experiments. Unbound sensitizer was removed by washing the cells once with culture medium, and the plates were illuminated at room temperature from the bottom ($\lambda$>650 nm, 12 J/cm$^2$). The light source was a 100 W Halogen lamp (Osram, Germany) equipped with a 4-cm water filter. The cultures were placed in the culture incubator and cell survival was determined 24 h after illumination, by Neutral Red viability assay. Three kinds of controls were used: (i) light control: cells illuminated in the absence of pigments; (ii) dark control: cells treated with pigments but kept in the dark; and (iii) untreated cells that were kept in the dark.

In Vivo Studies (iii) Tumor Implantation.

M2R or C6 cells (2×10$^6$) were implanted subcutaneously on the back of the mice; tumors developed to the treatment size (6-8 mm) within 2-3 weeks.

(iv) Preparation of Sensitizer.

Stock solutions of the compounds of the invention were prepared prior to use by dissolving the dry pigment directly in PBS to the desired concentration for injection.

(v) Biodistribution and Pharmacokinetics.

Pigment 4 of the invention (6 mg/kg body) was injected to CD1 nude mice via tail vein. Mice were sacrificed at the indicated times, and samples of the indicated organs or tissues were placed and weighed in pre-weighted vials and immediately frozen on dry ice. For examination, each sample was thawed and homogenized (1:10 w/v) in double-distilled water. Aliquots of the homogenate (0.5 ml) were lyophilized in Eppendorff test tubes. Then 0.2 ml of HNO$_3$ (70%, TraceSelect, Fluka) was added to each dry sample, incubated for 1 h at 90° C. and diluted in double-distilled water to 10 ml. Palladium concentrations were determined by ICP-MS. Background was determined for each organ/tissue on identical samples taken from untreated mice, and values were subtracted accordingly.

(vi) PDT Protocol.

The M2R tumor-bearing mice were anesthetized and the pigment was injected intravenously (i.v.) via the tail vein. The tumors were immediately illuminated transcutaneously for 5 min by 755 nm diode laser (CeramOptec, Germany) with light dose of either 30 J/cm2 (100 mW/cm2), 39 J/cm2 (130 mW/cm2) or 45 J/cm2 (150 mW/cm2). After the treatment, the mice were returned to the cage. In the dark control group, the mice were injected i.v. with sensitizer and placed in the dark cage for 24 h. In the light control group, the mice were illuminated with 45 J/cm$^2$.

(vii) Vascular Shutdown and Permeability.

Mice bearing C6 glioma tumor xenografts were treated with pigment 4 (9 mg/kg) and light (100 mW/cm$^2$ for 5 min) Immediately after treatment, Evans Blue (EB; 1% in PBS) was injected (0.5 ml, i.p.). Mice were photographed at 3 and 24 hours after treatment. The mice were sacrificed 24 hours after treatment and skin flap was made for each mouse and photographed. Then the tumor was removed with the skin above it, frozen for 1 hour at −20° C., and then axial slice was made and the slice was photographed. Control mice were injected with Evans Blue at the same time as the treated mice, and the protocol was continued as described above for all the mice together.

Example 14

Cytophotoxicity of the Sulfonated Bacteriochlorophyll Derivatives against Tumor Cell Cultures The phototoxicity of compounds 4 and 8 was determined as described in (ii) above in M2R mouse melanoma and H5V mouse endothelial cells. Cells were preincubated with increasing concentrations of the compound for 4 hours, washed and illuminated or kept in the dark.

Figure 1B:
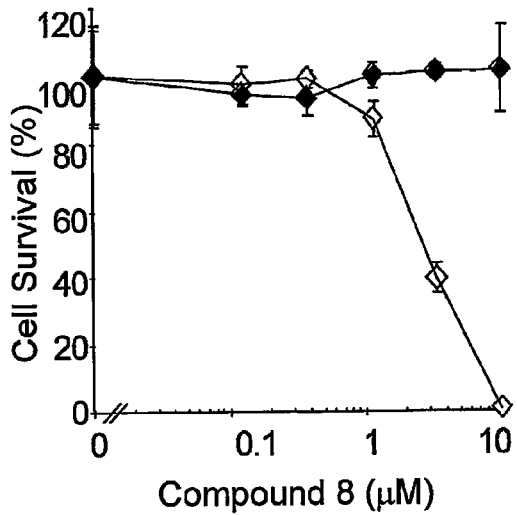
Figure 2A:
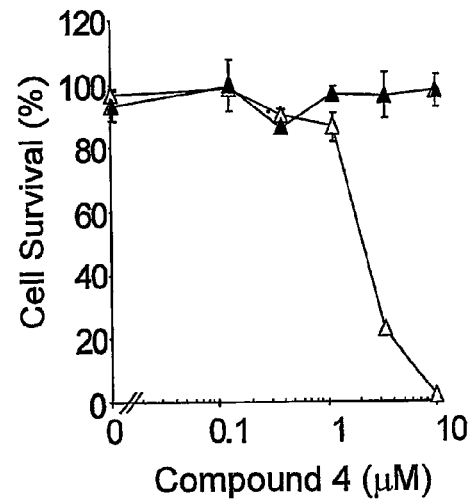
FIGS. 2A-2B are graphs showing the phototoxicity of the sulfonated compound 4 on H5V mouse endothelial cells (FIG. 2A) and M2R mouse melanoma cells (FIG. 2B). Cells were incubated with increasing concentrations of compound 4 for 4 hours, washed and illuminated (open shapes) or kept in the dark (dark control, closed shapes). Points are average of triplicates±STD.
Figure 2B:
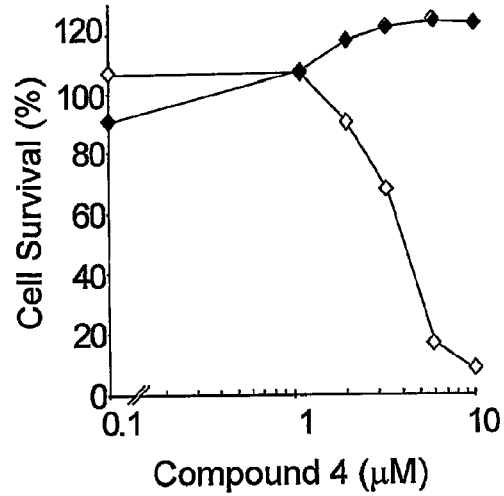

The results are shown in FIGS. 1A-1B for the bi-sulfonated compound 8 in H5V and MR2 cells, respectively, and in FIGS. 2A-2B for the mono-sulfonated compound 4 (comparison) in H5V and MR2 cells, respectively. As can be seen, the phototoxicity of both pigments 4 and 8 is concentration- and light-dependent, without any dark toxicity in the tested range. The $LD_{50}$ of both pigments is the same (~2 μM), and is similar in both cell lines.

Figure 3:
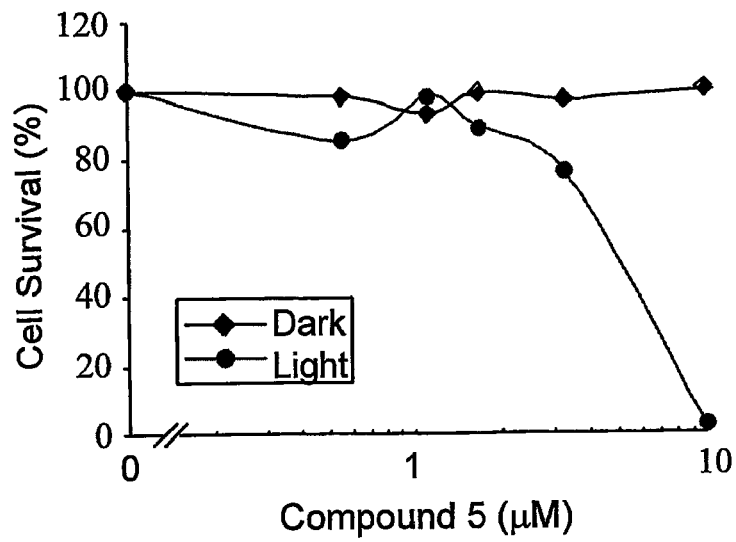
FIG. 3 is a graph showing the phototoxicity of the sulfonated compound 5 on M2R mouse melanoma cells. Cells were incubated with increasing concentrations of compound 5 for 4 hours, washed and illuminated (circles) or kept in the dark (dark control, diamonds). Points are average of triplicates.

The phototoxicity of the sulfonated pigments 5 and 11 was determined on M2R mouse melanoma cells. As can be seen in FIGS. 3 and 4, the phototoxicity of pigments 5 and 11 is concentration- and light-dependent, and the $LD_{50}$ of both pigments is the same (~5 μM). There is no dark toxicity within the tested range.

Example 15

Pharmacokinetics and Biodistribution of Compound 4

Figure 5:
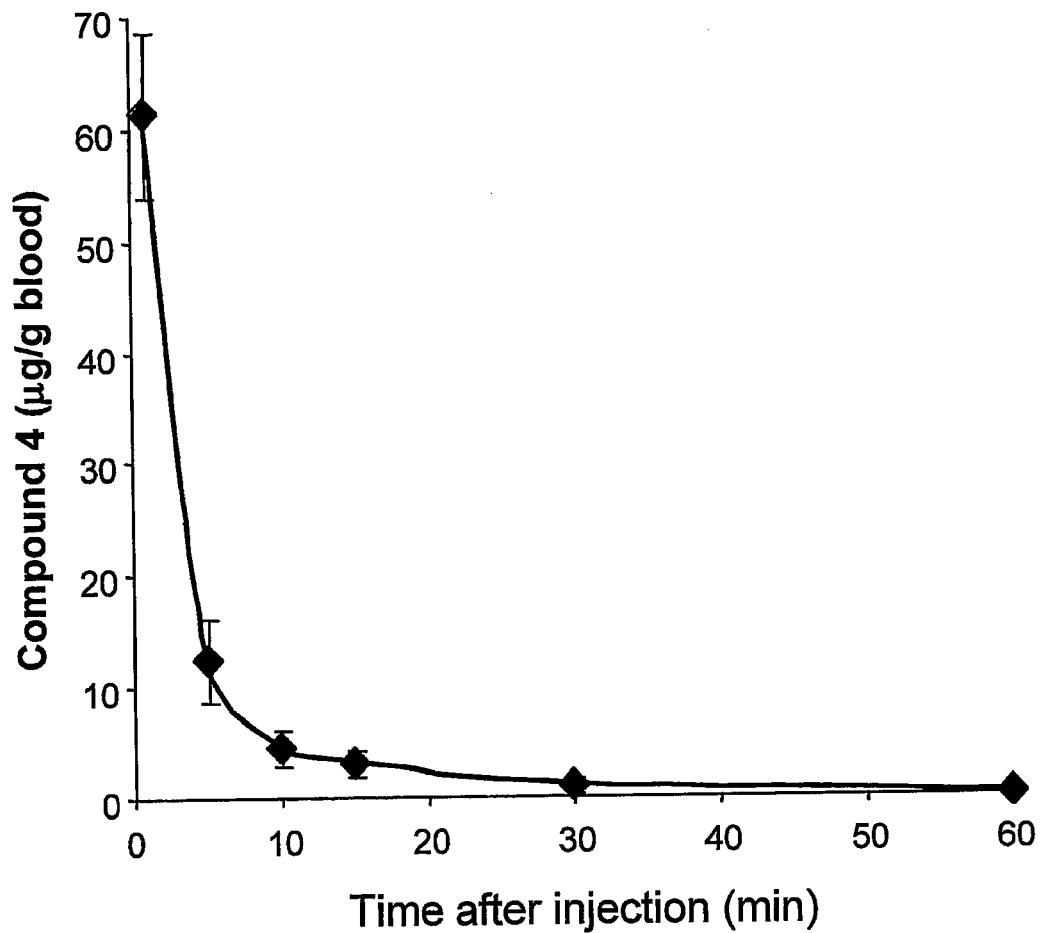
FIG. 5 is a graph showing pharmacokinetics of compound 4 in CD1 nude mice blood. Following compound 4 injection (6 mg/kg), blood samples were collected from the same mouse at the indicated times and Pd was determined. Each time point represents average of three mice±STD.

The first step before testing the phototoxicity of 4 toward PDT of solid melanoma xenografts was to determine the pigment's pharmacokinetics and biodistribution in vivo as described in section (vi) above. As can be seen in FIG. 5, about 90% of the pigment 4 cleared within the first 10-min after i.v. injection with a monophasic kinetic pattern with a $t_{0.5}$ of 1.65 min (Table 4). The fast clearance of 4 from the blood may imply that only a small fraction (if at all) is bound to the plasma components, otherwise clearance might have been slower.

TABLE 4

| Pharmacokinetic parameters of 4 in mice blood. | |
|---|---|
| Parameter | |
| Equation | y = 1.64 + 90.6e(−0.42t) |
| $T_{0.5}$ (min) | 1.65 |
| $K_{el}$ (min$^{-1}$) | 0.42 |
| Vd (ml) | 2.12 |
| CL (ml/min) | 0.89 |

$K_{el}$ - rate of elimination;
Vd - volume of distribution;
CL - clearance.

Figure 6:
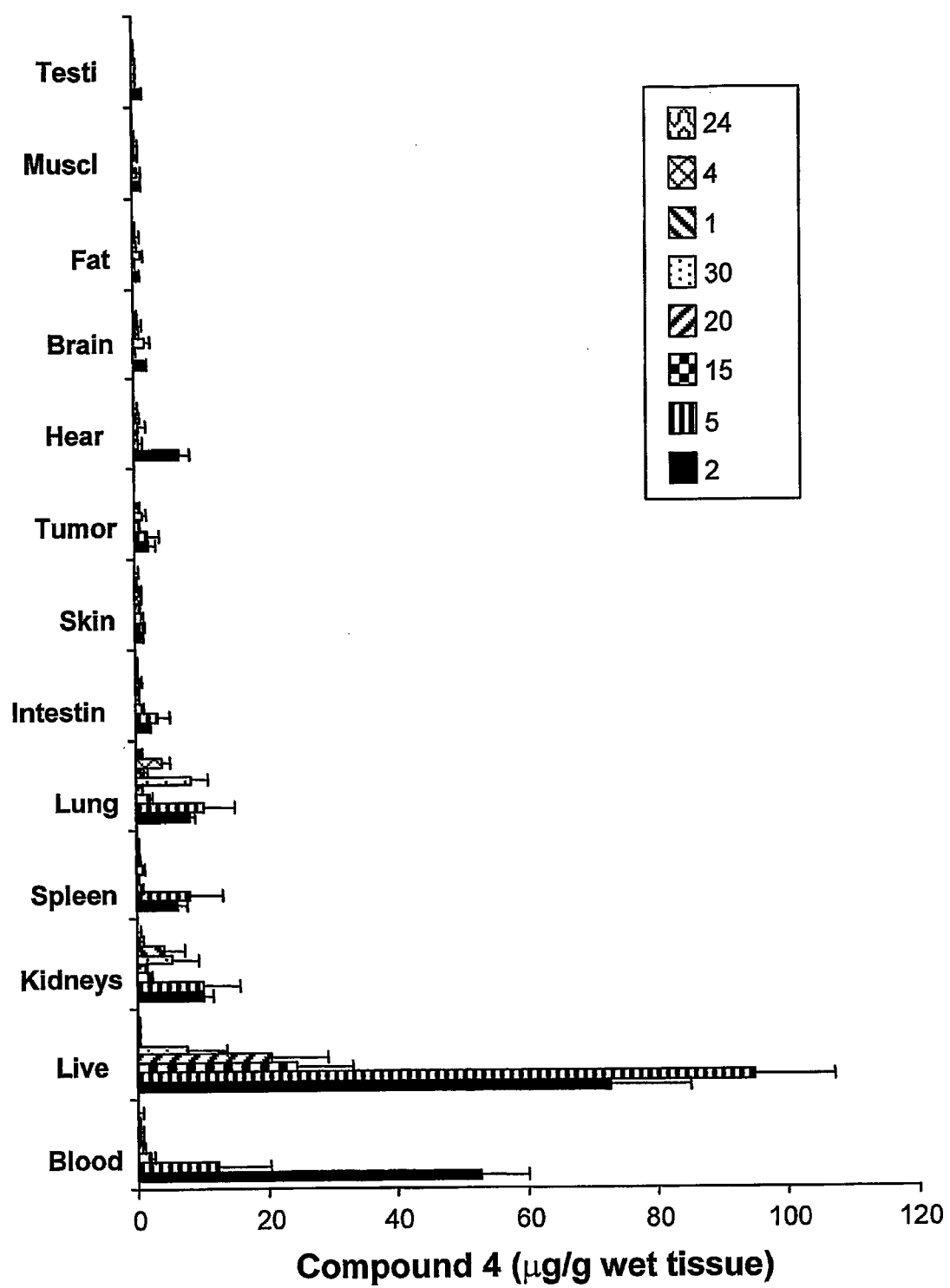
FIG. 6 shows biodistribution of compound 4 in CD1 nude mice. Mice were sacrificed at different times following compound 4 injection (6 mg/kg), and Pd content was determined for the indicated organs. Each time point represents average of three mice±STD.

The biodistribution of the compound 4 shows that, in most of the examined organs of the mouse, the pigment levels are high immediately after injection and drop to almost background levels within 20-30 min, similar to their clearance rates from the blood (FIG. 6). These results probably represent the pigment level in the blood trapped in the organ's vasculature as seen in spleen, lung, and heart. Furthermore, the results also suggest that pigment diffusion into the organs is negligible. The pigment 4 clears rapidly from the mouse body, and within 30 min after injection it is in background levels in all tissues. The clearance rate of 4 from the mouse body is much faster than Pd-Bpheid (1), which reaches background levels only 48 hours after injection (not shown).

Example 16

Photodynamic Treatment of M2R Melanoma Xenografts in CD1 Nude Mice with Sulfonated Pigment 4

Figure 7:
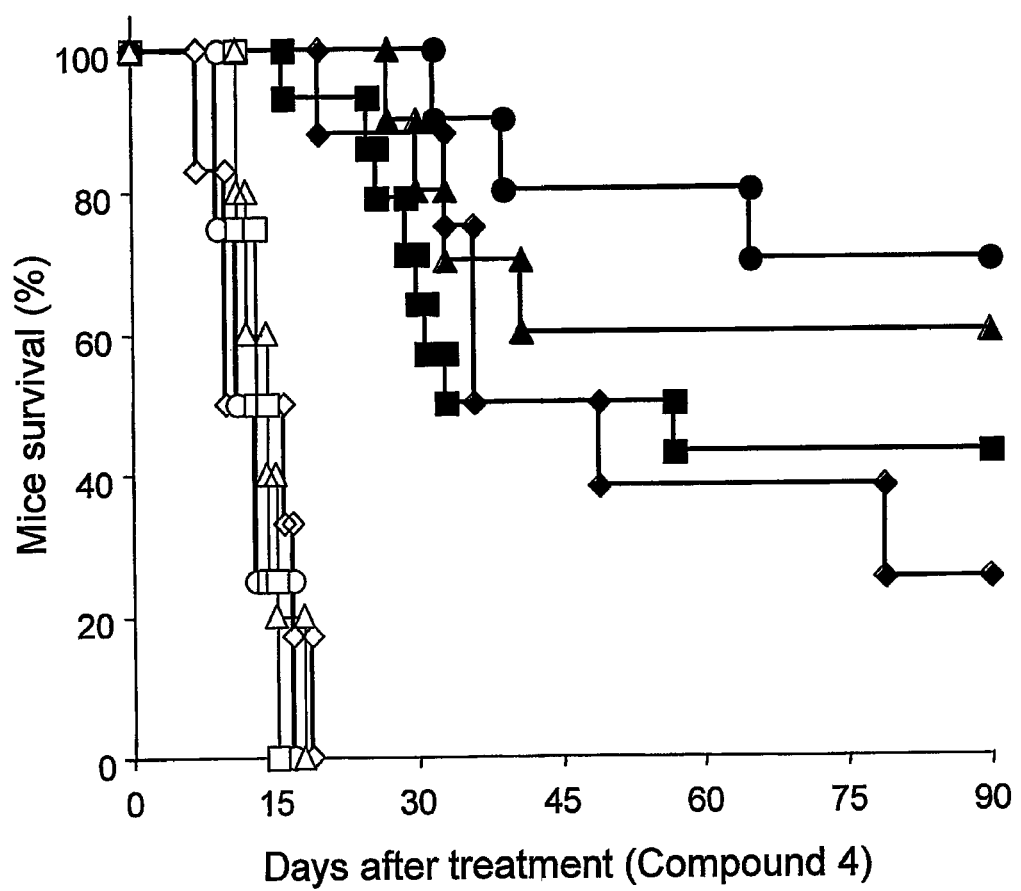
FIG. 7 shows PDT of melanoma xenografts with compound 4. Mice bearing M2R melanoma xenografts were intravenously injected with compound 4 (6 mg $kg^{-1}$) and illuminated for 5 min with light intensity of 30 $J/cm^2$ (n=14, filled squares), 39 $J/cm^2$ (n=8, filled diamonds) or 45 $J/cm^2$ (n=10, filled triangles). Mice that were injected with 9 mg $kg^{-1}$ of compound 4 were illuminated for 5 min with 30 $J/cm^2$ (n=10, filled circles). Control groups: untreated (n=4, open squares), dark control received 6 mg $kg^{-1}$ (n=4, open circles) or 9 mg $kg^{-1}$ (n=5, open triangles) of compound 4, and light control (n=6, open diamonds, 45 $J/cm^2$).
Figure 8A:
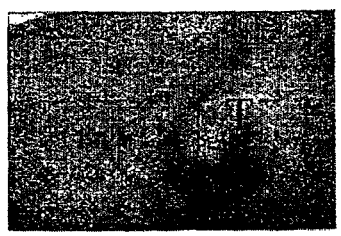
FIGS. 8a-8h are photographs showing the selective effect of PDT in mice bearing rat C6 glioma xenografts and treated with compound 4. (a-d) PDT treated animal; (e-h) untreated animal. (a) before treatment; (b) 3 hours after PDT and Evans-Blue (EB) injection; (c) skin flap of the treated area, 24 hours after PDT; (d) axial slice of the treated tumor 24 hours after PDT; (e) before EB injection; (f) 3 hours after EB injection; (g) skin flap 24 hours after EB injection; (h) axial slice of the untreated tumor, 24 hours after EB injection. T-tumor; S-skin; M-muscle; E-edema.
Figure 8E:
Figure 8B:
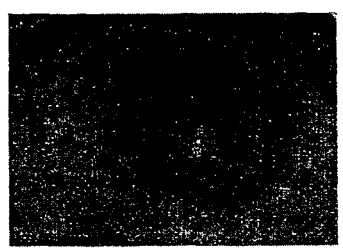
Figure 8F:
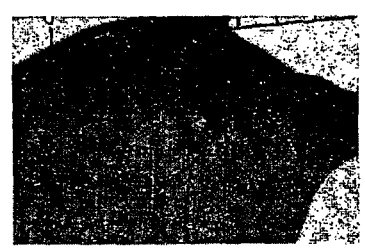
Figure 8C:
Figure 8G:
Figure 8D:
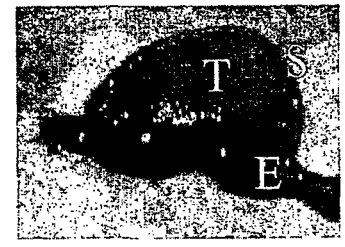
Figure 8H:
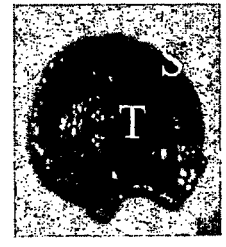
Figure 9A:
FIGS. 9A-9D show semi-thin sections of the lesion center and TEM 2 hours after occlusive PDT in a rabbit eye model with compound 4 (fluence 50 J/cm2, dose of 5 mg/Kg, and a DLI of 1 minute). Stasis and dilatation of choroidal vessels with relatively well preserved RPE cells and retina are observed (9A and 9B). TEM shows hemolysis of the red blood cells within the choriocapillary lumen (white arrows of 9D) and disrupted monocytes (white arrowhead). Bruch's membrane (Bm) is intact harboring well identified retinal pigment epithelium cells (RPE). Some of the choriocapillary endothelial cells are markedly altered demonstrating condensed chromatin (white star on 9C). Abbreviations: ONL: outer nuclear layer, ROS: rod outer segments, CC: Choriocappilaries, e: choriocapillary endothelial cells.
Figure 9B:
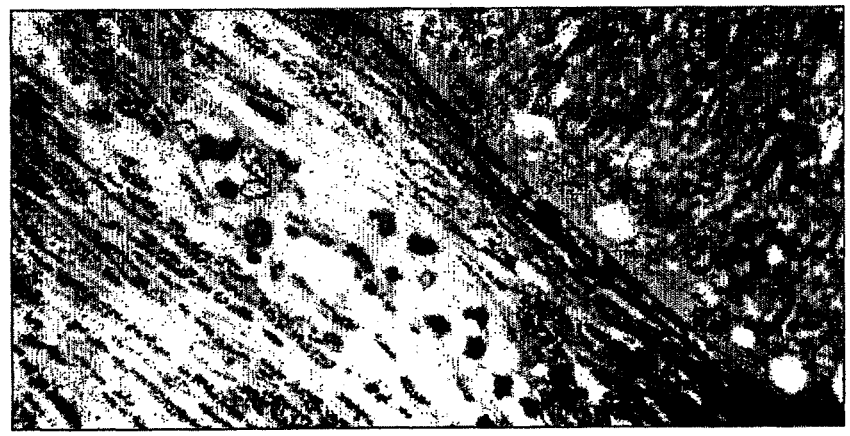
Figures 9C, 9D:
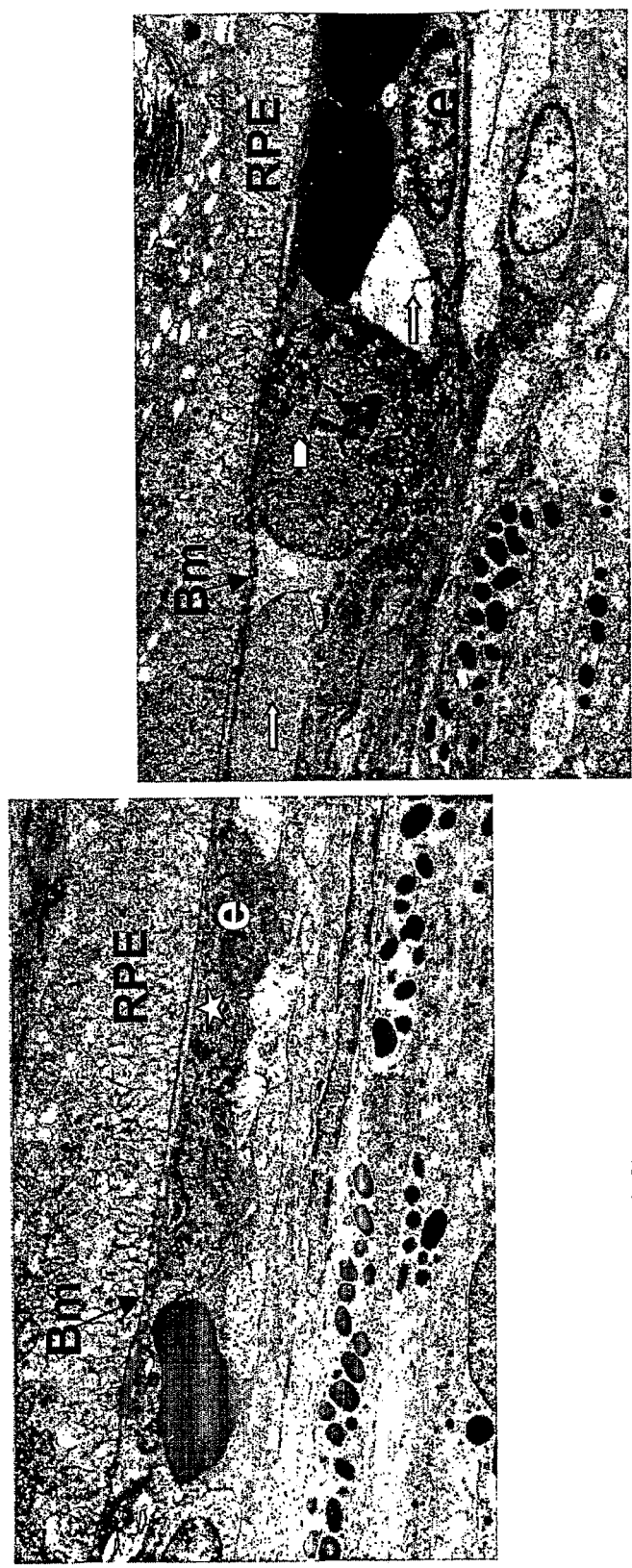

Based upon the pharmacokinetic results of Example 15 above, the treatment protocol for compound 4 was set to 5-min illumination immediately after pigment injection. In these experiments (see section (vii) above), a dedicated medical laser matched to the peak absorption of 4 (CeramOptec, Germany, 755 nm) was used. In order to determine the optimal drug/light protocol, mice were treated with drug dose of 6 mg/kg and increasing the light intensity (FIG. 7). As can be seen in the Kaplan-Meier survival curve, increasing the light intensity improves the mice cure rate from 43% to 60% with 30 and 45 J/cm$^2$, respectively. When the drug dose was elevated to 9 mg/kg with light intensity of 30 J/cm$^2$, there was a significant increase in the mice survival to 70% (FIG. 7). No dark toxicity was seen in animals treated with 6 or 9 mg/kg and kept in the dark.

Example 17

Selective Effect of Photodynamic Treatment with Compound 4

This experiment was carried out as described in section (vii) above. FIG. 8 illustrates the effect of photodynamic treatment on blood perfusion in C6 xenografts implanted in mice (a, e). Treated animal that was administrated with Evans-Blue immediately after PDT showed edema and enhanced vascular leakage of EB into the interstitium as demonstrated by the blue color (due to albumin-Evans Blue leakage) in the illuminated area when compared to the non-illuminated area in the same animal an to untreated animal (b, f). Twenty-four hours later, it can be seen that in the treated mice, the tumor surrounding is heavily colored blue (edema; c), while the tumor remains white (no EB color) due to vascular shutdown that occurred immediately after PDT (d). The muscle tissue under the tumor as well as the skin above and around the tumor (but within the treated area) is blue, indicating that no vascular shutdown took place (c, d). In the untreated animal, the tumor is colored blue like other tissues (g, h). The selective enclosure of new vessels in the tumor indicates that the compounds of the invention can be used for selective treatment of abnormal vasculature as in age-related macular degeneration (AMD).

Example 18

PDT treatment with Compound 4—Animal Model of AMD

Photodynamic therapy (PDT) has been developed aiming at inducing localized vascular occlusion of the newly formed vascular membranes emanating from the choroid (choroidal neovascularization—CNV). In age-related macular degeneration (AMD), PDT using verteporfin reduces the risk of visual loss secondary to CNV. The mechanism of action of PDT is thought to involve the release of reactive oxygen species which damage endothelial cells and activate sub endothelial clotting cascade. These events lead to the formation of thrombi within the vessel lumen.

For the treatment of choroidal neovascularization, highly selective parameters (Laser power density or fluence, photosensitizer dose, and distance to light illumination (DLI)) have been developed enabling precise focusing and targeting of the pathologic vessels and minimal secondary damaging effects to healthy retina and choroid tissues. However, using the only photosensitizer (verteporfin) presently available for clinical use, repeated treatments are generally required to achieve the desired CNV occlusive effects. Thus, the danger for collateral tissue damage is enhanced and may become a significant side effect of treatment.

In this experiment, we have evaluated the photodynamic treatment (PDT) potential of the hydrosoluble photosensitizer herein designated WST11 or compound 4, and compared its characteristics to those of verteporfin.

Compound 4 is a pure and stable bacteriochlorophyll derivative isolated as a black purple crystalline powder. It has a molecular weight of 916 and is soluble in aqueous solution. It is characterized by the following properties: (a) 4 main absorption peaks (750, 530, 385 and 330 nm). The strongest absorbance of light is near the infrared (≈750 nm) where tissue transmittance is the highest; (b) a very low cytotoxicity in the dark. Thus, tissue damage can be controlled by the light dose and length of exposure; (c) it is rapidly cleared from the body after administration. Therefore, potential skin photosensitization damage on exposure to ambient light or to the sun light is minimal; (d) generation of reactive oxygen species (ROS) is high because of efficient intersystem crossing (ISC).

The WST11 powder was diluted in endotoxin-free sterile water at a concentration of 10 mg/ml, and shaken until complete dissolution. This formulation remains stable for 24 hours at 4° C. protected from light. To calculate the volume to be injected, adjustment was made according to the rabbit weight. The appropriate volume solution was injected intravenously as a bolus via the marginal ear vein.

The potential of Compound 4 for PDT of age-related macular degeneration (AMD) was compared to verteporfin (Visudyne®, Novartis, Switzerland) using a rabbit eye model. Pigmented rabbits (136 "Fauve de Bourgogne" rabbits, 10-12 weeks old, 2.5-3 kg; Elevage des Pins, Epeigne-sur-Dême, France) were used. Acute and long term PDT effects on the rabbit eye were investigated for the following parameters: 1) 753 nm laser fluence (25 and 50 J/cm$^2$), Compound 4 (also designated WST11) doses (2.5 and 5 mg/kg) and distance to light illumination (DLI) of 1,5,10 and 15 minutes. 2) 689 nm laser fluence (10, 50, 100 J/cm$^2$), verteporfin doses (3, 6 and 12 mg/m$^2$) and a constant DLI of 5 min. These PDT parameters encompassed an array of effects on the choroid and the overlying retina were delivered for 83 seconds to induce occlusive, subthreshold occlusive and non-occlusive vascular events. Treated rabbit eyes were examined and followed by indirect ophthalmoscopy, fluorescein angiography (FA) and histology at various intervals after PDT. WST11 PDT using a fluence of 50 J/cm$^2$, 5 mg/kg drug dose and DLI of 1 minute induced total choroidal occlusion associated with structural lesions of the overlying RPE and retina in 100% of the treated eyes (FIGS. 9A-9D). Weaker, non-occlusive PDT parameters (25 J/cm$^2$, 5 mg/kg drug dose and DLI of 10 minutes) did not induce choriocapillaries occlusion nor retinal lesions. Verteporfin PDT using 12 mg/m$^2$ drug dose at a fluence of 100 J/cm$^2$ and DLI 5 minutes induced occlusive events (observed by FA) in 89% of the eyes and histology damage of the overlying retina and RPE layer in all eyes. Weaker non-occlusive verteporfin PDT parameters using 3 mg/m$^2$ drug dose, fluence 10 J/cm$^2$ and DLI 5 minutes did not induce any choriocapillaries occlusion on FA. However in these eyes, definite structural damage of the retina and choroid tissues were observed on histology. Similar to verteporfin, WST11 PDT induces transient occlusion of the choriocapillaries observed up to one week after treatment. Unlike Verteporfin, WST11 PDT parameters not inducing vessel occlusion do not cause RPE or retina structural damage. Thus, despite its capacity to induce vessel obstruction, WST11 PDT does not cause damage to the RPE and overlying retina when no occlusion of the choriocapillaries takes place. The advantages of these characteristics indicates that WST11 is a suitable candidate for PDT treatment of CNV in age-related macular degeneration.

For the histology, enucleated eyes were dissected under a binocular microscope. A 4 mm biopsy punch was used to excise the full thickness of treated zones. These tissues were fixed in glutaraldehyde, processed in cacodylate buffer and embedded in plastic. Semi-thin sections were obtained using a microtome and counter-stained with hematoxilin-eosin. These sections were analyzed using phase contrast microscopy. Specific sites of interest were further processed for TEM. Ultrathin sections were obtained using an ultramicrotome and counter-stained with uranyl acetate.

REFERENCES

Chen Q, Huang Z, Luck D, Beckers J, Brun P H, Wilson B C, Scherz A, Salomon Y, Hetzel F W. (2002) Preclinical studies in normal canine prostate of a novel palladium-bacteriopheophorbide (WST09) photosensitizer for photodynamic therapy of prostate cancers. *Photochem Photobiol.* 76(4):438-45.

Koudinova N V, Pinthus J H, Brandis A, Brenner O, Bendel P, Ramon J, Eshhar Z, Scherz A, Salomon Y. (2003) Photodynamic therapy with Pd-Bacteriopheophorbide (TOOKAD): successful in vivo treatment of human prostatic small cell carcinoma xenografts. *Int J Cancer* 104(6): 782-9.

Rosenbach-Belkin, V., Chen, L., Fiedor, L., Tregub, I., Pavlotsky, F., Brumfeld, V., Salomon, Y., Scherz, A. (1996) Serine conjugates of chlorophyll and bacteriochlorophyll: Photocytotoxicity in vitro and tissue distribution in mice bearing melanoma tumors. *Photochem. Photobiol.* 64:174-181.

Schreiber S, Gross S, Brandis A, Harmelin A, Rosenbach-Belkin V, Scherz A, Salomon Y. (2002) Local photodynamic therapy (PDT) of rat C6 glioma xenografts with Pd-bacteriopheophorbide leads to decreased metastases and increase of animal cure compared with surgery. *Int J Cancer.* 99(2):279-85.

Zilberstein, J., Schreiber, S., Bloemers, M C W M, Bendel, P., Neeman, M., Schechtman, E., Kohen, F., Scherz, A. Salomon, Y. (2001) Antivascular treatment of solid melanoma tumors with bacteriochlorophyll-serine-based photodynamic therapy. *Photochem. Photobiol.* 73:257-266.

Zilberstein, J., Bromberg, A., Franz, A., RosenbachBelkin, V., Kritzmann, A., Pfefermann, R., Salomon, Y., Scherz, A. (1997) Light-dependent oxygen consumption in bacteriochlorophyll-serine-treated melanoma tumors: On-line determination using a tissue-inserted oxygen microsensor. *Photochem. Photobiol.* 65: 1012-1019.

Scheme 1

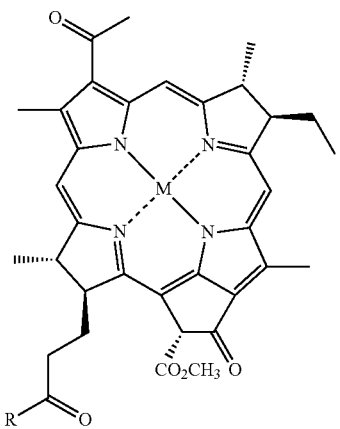

1: M = Mg, R = phytyl or geranylgeranyl (Bchl a)
R = Seryl (Bchl-Ser)

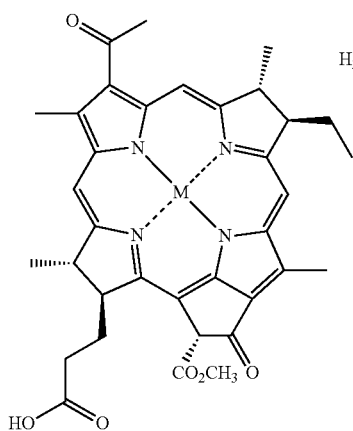

2: M = 2H
3: M = Pd

| sulfo NHS
| EDC
| DMSO

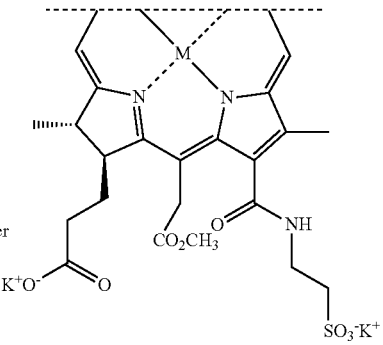

4: M = Pd
5: M = 2H
10: M = $Cu^{II}$
11: M = Zn
12: M = $Mn^{III}$

27
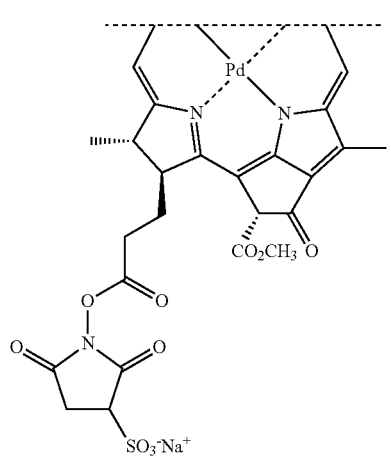
6
28
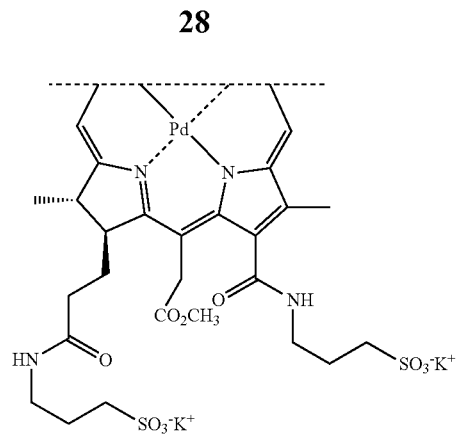
8
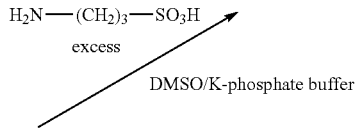
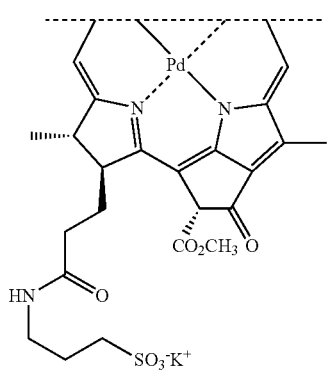
7
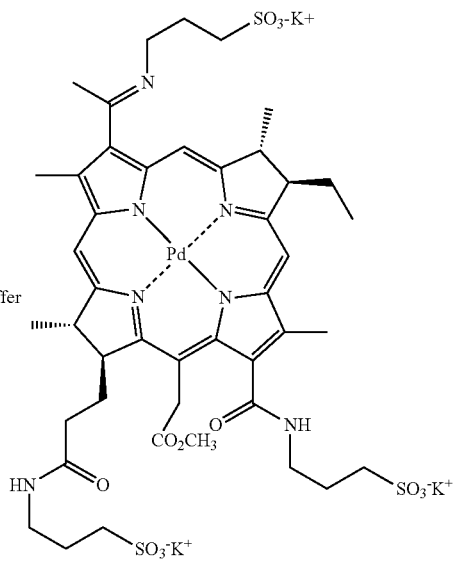
9
The invention claimed is:
1. A compound of formula I or II:
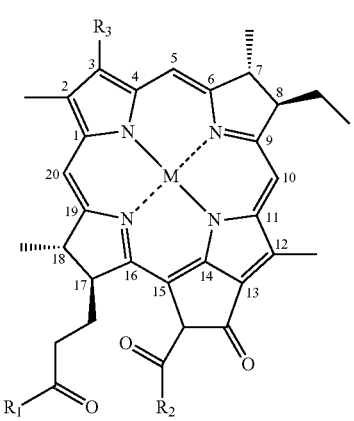
(I)
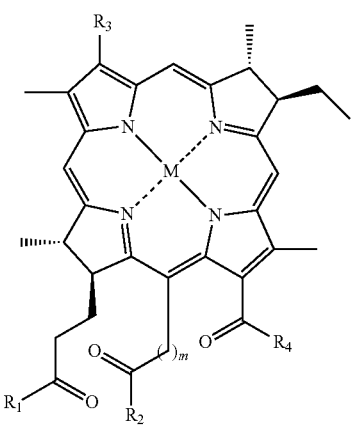
(II)
or a pharmaceutically acceptable salt thereof, wherein the compound contains at least one group having a negative charge at physiological pH, wherein
M represents 2H or a metal atom selected from divalent Pd, Pt, Co, Sn, Ni, Cu, Zn and Mn, and trivalent Fe, Mn and Cr;

$R_1$ and $R_4$ each independently is $Y—R_5$;

Y is O, S or $NR_5R_6$;

$R_2$ is $—OCH_3$;

$R_3$ is selected from $—CH=CH_2$, $—C(=O)—CH_3$, $—C(=O)—H$, $—CH=NR_7$, $—C(CH_3)=NR_7$, $—CH_2—OR_7$, $—CH_2—SR_7$, $—CH_2—NR_7R'_7$, $—CH(CH_3)—OR_7$, $—CH(CH_3)—SR_7$, $—CH(CH_3)—NR_7R'_7$, $—CH(CH_3)Hal$, $—CH_2$-Hal, $—CH_2—R_7$, $—CH=CR_7CR_7R'_7$, $—C(CH_3)=CR_7R'_7$, $—CH=CR_7Hal$, $—C(CH_3)=CR_7Hal$, and $—C≡CR_7$;

$R_5$, $R_6$, $R_7$ and $R'_7$ each independently is H or selected from the group consisting of:
(a) $C_1$-$C_{25}$ hydrocarbyl optionally containing one or more heteroatoms, phenyl moieties, or pyridyl moieties, each heteroatom individually selected from O, S, and N, wherein the $C_1$-$C_{25}$ hydrocarbyl is unsubstituted or substituted by one or more functional groups selected from the group consisting of halogen, oxo, OH, SH, CHO, $NH_2$, $CONH_2$, COOH, COSH, $SO_3H$, and $PO_3H_2$;
(b) a residue of an amino acid, a peptide or of a protein; and
(c) when Y is O or S, $R_5$ may further be $R_8^+$;

m is 0 or 1; and $R_8^+$ is $H^+$ or a cation;

provided that:
(i) at least one of $R_5$, $R_6$, $R_7$ and $R'_7$ is a $C_1$-$C_{25}$ hydrocarbyl substituted by a group selected from COOH, COSH, $SO_3H$, and $PO_3H_2$; or
(ii) at least one of $R_1$, $R_2$, and $R_4$ is OH, SH, $O^-R_8^+$ or $S^-R_8^+$;

excluding compounds of formula I and pharmaceutically acceptable salts thereof when $R_1$ is OH; and excluding compounds of formula II and pharmaceutically acceptable salts thereof devoid of a central metal atom and having a $—CH_2CH_2COOH$ group at position 17, a $—CH_2COOH$ or $—COOH$ group at position 15, a $—COOH$ group at position 13, methyl groups at positions 2, 7, 12, and 18, and ethyl groups at positions 3 and 8.

2. The compound of formula I or II according to claim 1, wherein $R_1$ is $Y—R_5$; Y is O, S or NH; and $R_5$ is a hydrocarbon chain substituted by a group selected from OH, SH, $SO_3H$, $NH_2$, $CONH_2$, COOH, COSH, and $PO_3H_2$.

3. The compound of formula I or II according to claim 1, wherein $R_5$ is the residue of an amino acid, a peptide or a protein.

4. The compound of formula I or II according to claim 1, wherein M is Pd.

5. The compound of formula I according to claim 1 wherein:
M is Pd;
$R_1$ is $—NH—(CH_2)_n—SO_3^-R_8^+$, $—NH—(CH_2)_n—COO^-R_8^+$; $—NH—(CH_2)_n—PO_3^{2-}(R_8^+)_2$;
$R_3$ is $—C(=O)—CH_3$;
$R_8^+$ is a monovalent cation such as $K^+$, $Na^+$, $Li^+$, $NH_4^+$; and
n is an integer from 1 to 10.

6. The compound of formula II according to claim 1 wherein:
M represents 2H, divalent Pd, Cu, or Zn or trivalent Mn;

$R_1$ is $—O^-R_8^+$, $—NH—(CH_2)_n—SO_3^-R_8^+$, $—NH—(CH_2)_n—COO^-R_8^+$; $—NH—(CH_2)_n—PO_3^{2-}(R_8^+)_2$; or $Y—R_5$ wherein Y is O, S or NH and $R_5$ is the residue of an amino acid, a peptide or a protein;

$R_3$ is $—C(=O)—CH_3$, $—CH=N—(CH_2)_n—SO_3^-R_8^+$; $—CH=N—(CH_2)_n—COO^-R_8^+$; $—CH=N—(CH_2)_n—PO_3^{2-}(R_8^+)_2$; $—CH_2—NH—(CH_2)_n—SO_3^-R_8^+$; $—NH—(CH_2)_n—COO^-R_8^+$; or $—NH—(CH_2)_n—PO_3^{2-}(R_8^+)_2$;

$R_4$ is $—NH—(CH_2)_n—SO_3^-R_8^+$; $—NH—(CH_2)_n—COO^-R_8^+$; $—NH—(CH_2)_n—PO_3^{2-}(R_{8+})_2$; $R_8^+$ is a monovalent cation selected from $K^+$, $Na^+$, $Li^+$, and $NH_4^+$; and m is 1, and n is an integer from 1 to 10, preferably 2 or 3.

7. The compound of formula II according to claim 1 wherein:

M is divalent Pd;

$R_1$ is $—O^-R_8^+$, $—NH—(CH_2)_n—SO_2^-R_8^+$, or $Y—R_5$ wherein Y is O, S or NH and $R_5$ is the residue of an amino acid, a peptide or a protein;

$R_3$ is $—C(=O)—CH_3$, $—CH=N—(CH_2)_n—SO_3^-R_3^+$; or $—CH_2—NH—(CH_2)_n—SO_3^-R_8^+$;

$R_4$ is $—NH—(CH_2)_n—SO_3^-R_8^+$; $NH—(CH_2)—COO^-R_8^+$; $NH—(CH_2)_n—PO_3^{2-}(R_8^+)_2$; $R_8^+$ is a monovalent cation;

m is 1, and n is 2 or 3.

8. The compound of formula I according to claim 5, which is Palladium bacteriopheophorbide a $17^3$-(3-sulfopropyl)amide, or a pharmaceutically acceptable salt thereof.

9. The compound of formula II according to claim 7, or a pharmaceutically acceptable salt thereof, wherein the compound is selected from the group consisting of:

$3^1$-oxo-15-methoxycarbonylmethyl-rhodobacteriochlorin $13^1$-(2-sulfoethyl)amide;

Palladium $3^1$-oxo-15-methoxycarbonylmethyl-rhodobacteriochlorin $13^1$,$17^3$-di(3-sulfopropyl)amide;

Palladium $3^1$-(3-sulfopropylimino)-15-methoxycarbonylmethyl-rhodobacteriochlorin $13^1$,$17^3$-di(3-sulfopropyl)amide;

Copper(II) $3^1$-oxo-15-methoxycarbonylmethyl-rhodobacteriochlorin $13^1$-(2-sulfoethyl)amide;

Zinc $3^1$-oxo-15-methoxycarbonylmethyl-rhodobacteriochlorin $13^1$-(2-sulfoethyl)amide;

Manganese(III) $3^1$-oxo-15-methoxycarbonylmethyl-rhodobacteriochlorin $13^1$-(2-sulfoethyl)amide;

Palladium $3^1$-oxo-15-methoxycarbonylmethyl-rhodobacteriochlorin $13^1$-(2-sulfoethyl)amide, $17^3$-(N-immunoglobulin G)amide;

Palladium $3^1$-oxo-15-methoxycarbonylmethyl-rhodobacteriochlorin $13^1$-(2-carboxy-ethyl)amide;

Palladium $3^1$-oxo-15-methoxycarbonylmethyl-rhodobacteriochlorin $13^1$-(3-phosphopropyl)amide; and Palladium $3^1$-(3-sulfopropylamino)-15-methoxycarbonylmethyl-rhodobacteriochlorin $13^1$,$17^3$-di(3-sulfopropyl)amide.

10. A compound of formula I or II:

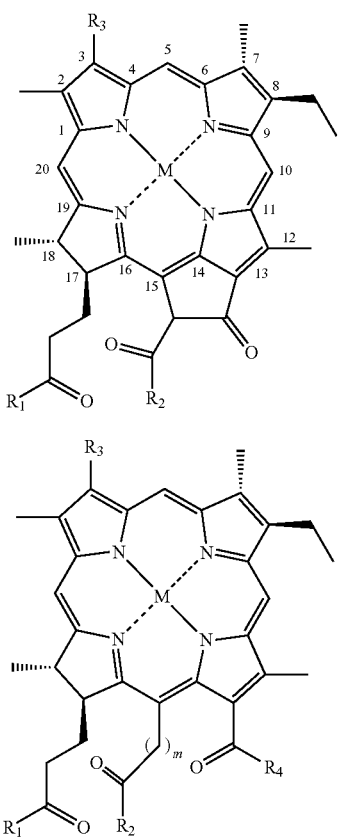

or a pharmaceutically acceptable salt thereof,
wherein the compound contains at least one group having a negative charge at physiological pH,
wherein
M represents 2H or a metal atom selected from divalent Pd, Pt, Co, Sn, Ni, Cu, Zn and Mn, and trivalent Fe, Mn and Cr;
$R_1$, $R_2$, and $R_4$ each independently is Y—$R_5$;
Y is O, S or $NR_5R_6$;
$R_3$ is selected from —CH=$CH_2$, —C(=O)—$CH_3$, —C(=O)—H, —CH=$NR_7$, —C($CH_3$)=$NR_7$, —$CH_2$—$OR_7$, —$CH_2$—$SR_7$, —$CH_2$—$NR_7R'_7$, —CH($CH_3$)—$OR_7$, —CH($CH_3$)—$SR_7$, —CH($CH_3$)—$NR_7R'_7$, —CH($CH_3$)Hal, —$CH_2$-Hal, —$CH_2$—$R_7$, —CH=$CR_7CR_7R'_7$, —C($CH_3$)=$CR_7R'_7$, —CH=$CR_7$Hal, —C($CH_3$)=$CR_7$Hal, and —C≡$CR_7$;
$R_5$, $R_6$, $R_7$ and $R'_7$ each independently is selected from the group consisting of:
(a) $C_1$-$C_{25}$ hydrocarbyl optionally containing one or more heteroatoms, phenyl moieties, or pyridyl moieties, each heteroatom individually selected from O, S, and N, wherein the $C_1$-$C_{25}$ hydrocarbyl is unsubstituted or substituted by one or more functional groups selected from the group consisting of halogen, oxo, OH, SH, CHO, $NH_2$, $CONH_2$, COOH, COSH, $SO_3H$, and $PO_3H_2$; and
(b) a residue of an amino acid, a peptide or of a protein; and
(c) when Y is S, $R_5$ may further be $R_8^+$;

m is 0 or 1; and
$R_8^+$ is $H^+$ or a cation;
provided that:
(i) at least one of $R_5$, $R_6$, $R_7$ and $R'_7$ is a $C_1$-$C_{25}$ hydrocarbyl substituted by a group selected from COOH, COSH, $SO_3H$, and $PO_3H_2$; or
(ii) at least one of $R_1$, $R_2$, and $R_4$ is SH, or $S^-R_8^+$.

11. A compound selected from the group consisting of:
$3^1$-oxo-15-methoxycarbonylmethyl-rhodobacteriochlorin $13^1$-(2-sulfoethyl)amide dipotassium salt;
Palladium $3^1$-oxo-15-methoxycarbonylmethyl-rhodobacteriochlorin $13^1$,$17^3$-di(3-sulfopropyl)amide dipotassium salt;
Palladium $3^1$-(3-sulfopropylimino)-15-methoxycarbonylmethyl-rhodobacteriochlorin $13^1$,$17^3$-di(3-sulfopropyl)amide tripotassium salt;
Copper(II) $3^1$-oxo-15-methoxycarbonylmethyl-rhodobacteriochlorin $13^1$-(2-sulfoethyl)amide dipotassium salt;
Zinc $3^1$-oxo-15-methoxycarbonylmethyl-rhodobacteriochlorin $13^1$-(2-sulfoethyl)amide dipotassium salt;
Manganese(III) $3^1$-oxo-15-methoxycarbonylmethyl-rhodobacteriochlorin $13^1$-(2-sulfoethyl)amide dipotassium salt;
Palladium $3^1$-oxo-15-methoxycarbonylmethyl-rhodobacteriochlorin $13^1$-(2-sulfoethyl)amide, $17^3$-(N-immunoglobulin G) amide potassium salt;
Palladium $3^1$-oxo-15-methoxycarbonylmethyl-rhodobacteriochlorin $13^1$-(2-carboxy-ethyl)amide dipotassium salt;
Palladium $3^1$-oxo-15-methoxycarbonylmethyl-rhodobacteriochlorin $13^1$-(3-phosphopropyl)amide tripotassium salt; and
Palladium $3^1$-(3-sulfopropylamino)-15-methoxycarbonylmethyl-rhodobacteriochlorin $13^1$,$17^3$-di(3-sulfopropyl)amide tripotassium salt.

12. Palladium bacteriopheophorbide a $17^3$-(3-sulfo-1-oxysuccinimide) ester, or a pharmaceutically acceptable salt thereof.

13. A method for preparing a compound of formula II according to claim 1 wherein
$R_1$ is —$O^-R_8^+$; $R_3$ is acetyl; $R_4$ is —NH—$(CH_2)_n$—$SO_3^-$ $R_8^+$, $R_8^+$ is a monovalent cation; m is 1 and n is 1 to 10, which comprises:
(i) reacting the corresponding M-bacteriopheophorbide of formula I wherein $R_1$ is OH with an aminosulfonic acid of the formula $H_2N$—$(CH_2)_n$—$SO_3H$ in a $R_8^+$-buffer; and
(ii) isolating the desired compound of formula II.

14. Palladium bacteriopheophorbide a $17^3$-(3-sulfopropyl)amide potassium salt.

15. Palladium bacteriopheophorbide a $17^3$-(3-sulfo-1-oxysuccinimide)ester sodium salt.

16. A pharmaceutical composition comprising a compound according to claim 1 and a pharmaceutically acceptable carrier.

17. A method for preparing a compound of formula II according to claim 1 wherein $R_1$ is —$O^-R_8^+$; $R_3$ is acetyl; $R_4$ is —NH—$(CH_2)_n$—$COO^-R_8^+$; $R_8^+$ is a monovalent cation; m is 1 and n is 1 to 10, which comprises:
(i) reacting (a) the corresponding M-bacteriopheophorbide of formula I wherein $R_1$ is OH with (b) an aminocarboxylic acid of the formula $H_2N$—$(CH_2)$—COOH in a $R_8^+$-buffer; and
(ii) isolating the desired compound of formula II.

18. A method for preparing a compound of formula II according to claim 1 wherein $R_1$ is —$O^-R_8^+$; $R_3$ is acetyl; $R_4$ is —NH—$(CH_2)_n$—$PO_3^{2-}(R_8^+)_2$; $R_8^+$ is a monovalent cation; m is 1 and n is 1 to 10, which comprises:
  (i) reacting (a) the corresponding M-bacteriopheophorbide of formula I wherein $R_1$ is OH with (b) an aminophosphonic acid of the formula $H_2N$—$(CH_2)_n$—$PO_3H_2$ in a $R_8^+$-buffer; and
  (ii) isolating the desired compound of formula II.

19. A method for preparing a compound of formula II according to claim 1 wherein $R_1$ and $R_4$ contain the same group having a negative charge at physiological pH, which comprises:
  reacting (a) the corresponding M-bacteriopheophorbide of formula I with an excess of an aminosulfonic, aminocarboxylic or aminophosphonic acid in a $R_8^+$-buffer; and
  (ii) isolating the desired 13,17-disubstituted derivative of formula II.

20. A method for preparing a compound of formula II in claim 1 wherein $R_1$ and $R_4$ are each —NH—$(CH_2)_n$—$SO_3^-R_8^+$; $R_3$ is acetyl; $R_8^+$ is a monovalent cation; m is 1 and n is 1 to 10, which comprises:
  (i) coupling the corresponding M-bacteriopheophorbide of formula I wherein $R_1$ is OH with N-hydroxy-sulfosuccinimide (sulfo NHS) in the presence of 1-ethyl-3-(3-dimethylaminopropyl)-carbodiimide (EDC);
  (ii) reacting the resulting M-bacteriopheophorbide-$17^3$-N-hydroxy-sulfosuccinimide ester with an excess of an aminosulfonic acid of the formula $H_2N(CH_2)_n$—$SO_3H$ in a $R_8^+$-buffer, thus obtaining a compound of formula I having a —NH—$(CH_2)_n$—$SO_3^-R_8^+$ at position 17;
  (iii) reacting the product of step (ii) with an excess of $H_2N$—$(CH_2)_n$—$SO_3H$ in a $R_8^+$-buffer; and
  (iv) isolating the desired compound of formula II.

21. A method for preparing a compound of formula II according to claim 1 wherein $R_1$ and $R_4$ are each —$NH(CH_2)_n$—$COO^-R_8^+$; $R_3$ is acetyl; $R_8^+$ is a monovalent cation; m is 1 and n is 1 to 10, which comprises:
  (i) coupling the corresponding M-bacteriopheophorbide of formula I wherein $R_1$ is OH with N-hydroxy-sulfosuccinimide (sulfo NHS) in the presence of 1-ethyl-3-(3-dimethylaminopropyl)-carbodiimide (EDC);
  (ii) reacting the resulting M-bacteriopheophorbide-$17^3$-N-hydroxy-sulfosuccinimide ester with an excess of an aminocarboxylic acid of the formula $H_2N$—$(CH_2)$—COOH in a $R_8^+$-buffer, thus obtaining a compound of formula I having a —NH—$(CH_2)_n$—$COO^-R_8^+$ at position 17;
  (iii) reacting the product of step (ii) with an excess of $H_2N$—$(CH_2)_n$—COOH in a $R_8^+$-buffer; and
  (iv) isolating the desired compound of formula II.

22. A method for preparing a compound of formula II according to claim 1 wherein $R_1$ and $R_4$ are each a group —$NH_2$—$(CH_2)_n$—$PO_3^{2-}R_8^+$; $R_3$ is acetyl; $R_8^+$ is a monovalent cation; m is 1 and n is 1 to 10, which comprises:
  (i) coupling the corresponding M-bacteriopheophorbide of formula I wherein $R_1$ is OH with N-hydroxy-sulfosuccinimide (sulfo NHS) in the presence of 1-ethyl-3-(3-dimethylaminopropyl)-carbodiimide (EDC);
  (ii) reacting the resulting M-bacteriopheophorbide-$17^3$-N-hydroxysulfosuccinimide ester with an excess of an aminophosphonic acid of the formula $H_2N$—$(CH_2)_n$—$PO_3H_2$ in a $R_8^+$-buffer, thus obtaining a compound of formula I having a —$NH_2$—$(CH_2)_n$—$PO_3^{2-}R_8^+$ at position 17;
  (iii) reacting the product of step (ii) with an excess of $H_2N$—$(CH_2)_n$—$PO_3H_2$ in a $R_8^+$-buffer; and
  (iv) isolating the desired compound of formula II.

23. A method for tumor photodynamic therapy of a which comprises:
  (a) administering the compound according to claim 1 to an individual having a tumor; and
  (b) locally irradiating the tumor with light of an appropriate wavelength.

24. A method for photodynamic therapy of age-related macular degeneration by vascular occlusion, which comprises: (a) administering the compound according to claim 1 to an individual in need thereof; and (b) irradiating the local area of the macular degeneration with light of an appropriate wavelength.

25. A method for tumor diagnosis which comprises:
  (a) administering to a subject suspected of having a tumor the compound according to claim 1; and
  (b) irradiating the subject with light of an appropriate wavelength and measuring the fluorescence of the suspected area, wherein a higher fluorescence indicates tumor sites.

26. A method for photodynamic therapy of benign prostate hypertrophy, which comprises:
  (a) administering to an individual in need the compound according to claim 1; and
  (b) locally irradiating the prostate with light of an appropriate wavelength.

* * * * *

UNITED STATES PATENT AND TRADEMARK OFFICE
CERTIFICATE OF CORRECTION

PATENT NO. : 8,461,142 B2
APPLICATION NO. : 12/942938
DATED : June 11, 2013
INVENTOR(S) : Avigdor Scherz et al.

It is certified that error appears in the above-identified patent and that said Letters Patent is hereby corrected as shown below:

In the Claims:

In column 29, line 15

[-CH$_2$-R$_7$, -CH=CR$_7$CR$_7$R'$_7$, -C(CH$_3$)]

should read

-- -CH$_2$-R$_7$, -CH=CR$_7$R'$_7$, -C(CH$_3$) --

In column 30, line 20

[ m is 1, and n is an integer from 1 to 10, preferably 2 or 3.]

should read

-- m is 1, and n is an integer from 1 to 10. --

In column 31, line 52

[-CH$_2$-R$_7$, -CH=CR$_7$CR$_7$R'$_7$, -C(CH$_3$)]

should read

-- -CH$_2$-R$_7$, -CH=CR$_7$R'$_7$, -C(CH$_3$) --

In column 32, line 37

[Palladium bacteriopheophorbide a 17$^3$–(3-sulfo-1-ox- ]

should read

-- Palladium bacteriopheophorbide a 17$^3$–(3-sulfo-1-oxy- --

Signed and Sealed this
Seventeenth Day of September, 2013

Teresa Stanek Rea
*Deputy Director of the United States Patent and Trademark Office*

In column 32, line 38

[ysuccinimide) ester, or a pharmaceutically acceptable salt]

should read

-- succinimide) ester, or a pharmaceutically acceptable salt --

In column 32, line 52

[ Palladium bacteriopheophorbide a $17^3$–(3-sulfo-1-ox- ]

should read

-- Palladium bacteriopheophorbide a $17^3$–(3-sulfo-1-oxy- --

In column 32, line 53

[ysuccinimide) ester, sodium salt ]

should read

-- succinimide) ester, sodium salt --

In column 33, line 35

[ -NH($CH_2$)$_n$-COO$^-$$R_8^+$; $R_3$ is acetyl; $R_8^+$ is a monovalent ]

Should read

-- -NH-($CH_2$)$_n$-COO$^-$$R_8^+$; $R_3$ is acetyl; $R_8^+$ is a monovalent --

In column 33, line 43

[ aminocarboxylic acid of the formula $H_2$N-($CH_2$)- ]

Should read

-- aminocarboxylic acid of the formula $H_2$N-($CH_2$)$_n$- --

In column 34, line 21

[ A method for tumor photodynamic therapy of a which]

Should read

-- A method for photodynamic therapy of a tumor which --